(12) United States Patent
Kermode et al.

(10) Patent No.: US 8,790,242 B2
(45) Date of Patent: Jul. 29, 2014

(54) VENTRICULAR VOLUME REDUCTION

(75) Inventors: James R. Kermode, Los Altos, CA (US); Miles D. Alexander, Sunnyvale, CA (US); Michael P. Boutillette, San Francisco, CA (US); Matthew T. Davila, Sunnyvale, CA (US); Irene Bing Bie Tan, San Jose, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 874 days.

(21) Appl. No.: 12/912,632

(22) Filed: Oct. 26, 2010

(65) Prior Publication Data
US 2011/0098525 A1    Apr. 28, 2011

Related U.S. Application Data

(60) Provisional application No. 61/255,018, filed on Oct. 26, 2009.

(51) Int. Cl.
*A61F 2/00* (2006.01)
(52) U.S. Cl.
USPC .............................. 600/37; 600/16
(58) Field of Classification Search
USPC ................................. 600/37, 16–18
See application file for complete search history.

(56) References Cited

U.S. PATENT DOCUMENTS

| | | | |
|---|---|---|---|
| 3,874,388 A | 4/1975 | King et al. |
| 4,007,743 A | 2/1977 | Blake |
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |

(Continued)

FOREIGN PATENT DOCUMENTS

| | | |
|---|---|---|
| JP | H08257031 A | 10/1996 |
| JP | 2003512128 A | 4/2003 |

(Continued)

OTHER PUBLICATIONS

Khairkhahan Alexander; U.S. Appl. No. 13/129,961 entitled "Devices and methods for delivering an endocardial device," filed Jul. 14, 2011.
Boersma et al.; Early thrombolytic treatment in acute myocardial infarction: reappraisal of the golden hour; Lancet: vol. 348; pp. 771-775; 1996.
Sharkey et al.; Left ventricular apex occluder. Description of a a ventricular partitioning device; EuroInterv.; 2(1); pp. 125-127; May 2006.

(Continued)

*Primary Examiner* — John Lacyk
(74) *Attorney, Agent, or Firm* — Shay Glenn LLP

(57) ABSTRACT

Devices and systems including implants (which may be removable) and methods of using them for reducing ventricular volume. The implants described herein are cardiac implants that may be inserted into a patient's heart, particularly the left ventricle. The implant may support the heart wall, or may be secured to the heart wall. The implants are typically ventricular partitioning device for partitioning the ventricle into productive and non-productive regions in order to reduce the ventricular volume.

8 Claims, 33 Drawing Sheets

(56) References Cited

U.S. PATENT DOCUMENTS

| | | |
|---|---|---|
| 5,192,314 A | 3/1993 | Daskalakis |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,320,665 B2 | 1/2008 | Vijay |
| 7,399,271 B2 | 7/2008 | Khairkhahan et al. |
| 7,485,088 B2 | 2/2009 | Murphy et al. |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,762,943 B2 | 7/2010 | Khairkhahan |
| 7,862,500 B2 | 1/2011 | Sharkey et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0078671 A1 | 4/2003 | Lesniak et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |

(56) References Cited

U.S. PATENT DOCUMENTS

| | | |
|---|---|---|
| 2004/0122090 A1 | 6/2004 | Lipton |
| 2004/0127935 A1 | 7/2004 | Van Tassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1* | 3/2006 | Raman et al. ............. 600/37 |
| 2006/0069430 A9* | 3/2006 | Rahdert et al. ............. 623/2.36 |
| 2006/0079736 A1 | 4/2006 | Chin et al. |
| 2006/0116692 A1 | 6/2006 | Ward |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0264980 A1 | 11/2006 | Khairkhahan et al. |
| 2006/0276684 A1 | 12/2006 | Speziali |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0071298 A1 | 3/2008 | Khairkhahan et al. |
| 2008/0228805 A1 | 9/2008 | Bruck et al. |
| 2008/0293996 A1 | 11/2008 | Evans et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0187063 A1 | 7/2009 | Khairkhahan |
| 2009/0254195 A1 | 10/2009 | Khairkhahan et al. |
| 2009/0287040 A1 | 11/2009 | Khairkhahan et al. |
| 2010/0048987 A1 | 2/2010 | Khairkhahan et al. |
| 2010/0121132 A1 | 5/2010 | Nikolic et al. |
| 2010/0262168 A1 | 10/2010 | Khairkhahan et al. |
| 2010/0274227 A1 | 10/2010 | Khairkhahan et al. |
| 2011/0178362 A1 | 7/2011 | Evans et al. |
| 2012/0259356 A1 | 10/2012 | Khairkhahan |
| 2013/0090677 A1 | 4/2013 | Evans et al. |
| 2013/0165735 A1 | 6/2013 | Khairkhahan et al. |
| 2013/0317537 A1 | 11/2013 | Khairkhahan |
| 2013/0338695 A1 | 12/2013 | Nikolic et al. |

FOREIGN PATENT DOCUMENTS

| | | |
|---|---|---|
| JP | 2003512129 A | 4/2003 |
| WO | WO 96/37859 A1 | 11/1996 |
| WO | WO 98/03213 A1 | 1/1998 |
| WO | WO 00/27292 | 5/2000 |
| WO | WO 00/42919 A1 | 7/2000 |
| WO | WO 00/50639 A2 | 8/2000 |
| WO | WO 01/30266 | 5/2001 |
| WO | WO 01/78625 | 10/2001 |
| WO | WO 02/30335 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 | 1/2003 |
| WO | WO 03/043507 A2 | 5/2003 |
| WO | WO 03/073961 A1 | 9/2003 |
| WO | WO 03/090716 A1 | 11/2003 |
| WO | WO 03/099300 A1 | 12/2003 |
| WO | WO 03/099320 A1 | 12/2003 |
| WO | WO 03/103538 A1 | 12/2003 |
| WO | WO 03/103743 A2 | 12/2003 |
| WO | WO 2004/012629 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2007/092354 | 8/2007 |

OTHER PUBLICATIONS

U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).

Alexander, Miles; U.S. Appl. No. 13/827,927 entitled "Systems and methods for making a laminar ventricular partitioning device," filed Mar. 14, 2013.

Kermode et al.; U.S. Appl. No. 13/828,184 entitled "Devices and methods for delivering an endocardial device," filed Mar. 14, 2013.

AGA Medical Corporation. www.amplatzer.com/products. "The Muscular VSD Occluder" and "The Septal Occluder" device description. Accessed Apr. 3, 2002.

Artrip et al.; Left ventricular volume reduction surgery for heart failure: A physiologic perspective; J Thorac Cardiovasc Surg; vol. 122; No. 4; pp. 775-782; 2001.

Di Mattia, et al. Surgical treatment of left ventricular post-infarction aneurysm with endoventriculoplasty: late clinical and functioal results. European Journal of Cardio-thoracic Surgery. 1999; 15:413-418.

Dor, et al. Ventricular remodeling in coronary artery disease. Current Opinion in Cardiology. 1997; 12:533-537.

Dor, V. The treatment of refractory ischemic ventricular tachycardia by endoventricular patch plasty reconstruction of the left ventricle. Seminars in Thoracic and Cardiovascular Surgery. 1997; 9(2): 146-155.

Dor. Surgery for left ventricular aneurysm. Current Opinion in Cardiology. 1990; 5: 773-780.

Gore Medical. www.goremedical.com. "Helex Septal Occluder" product description. Accessed Apr. 3, 2002.

Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.

Katsumata, et al. An objective appraisal of partial left ventriculectomy for heart failure. Journal of Congestive Heart Failure and Circulator Support. 1999; 1(2): 97-106.

Kawata, et al. Systolic and Diastolic Function after Patch Reconstruction of Left Ventricular Aneurysms. Ann. Thorac. Surg. 1995; 59:403-407.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Boutillette et al.; U.S. Appl. No. 12/893,832 entitled "Devices and methods for delivering an endocardial device," filed Sep. 29, 2010.

* cited by examiner

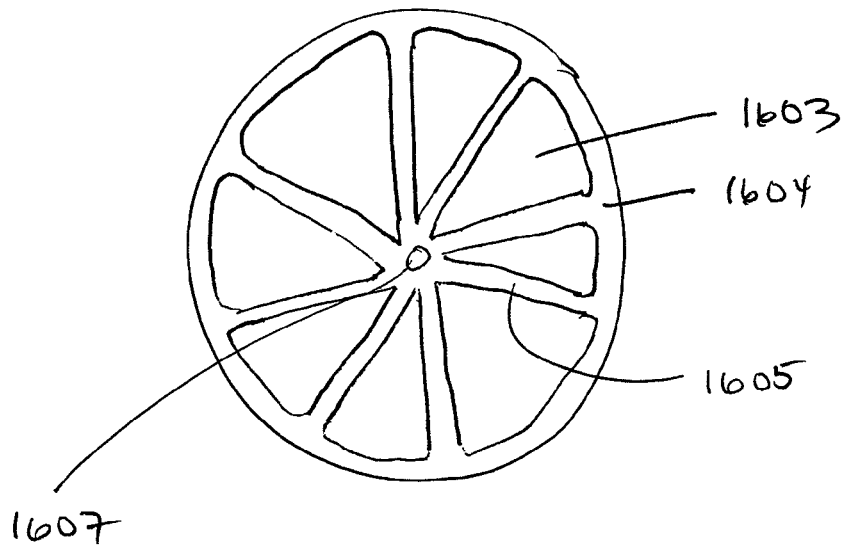
Fig. 16
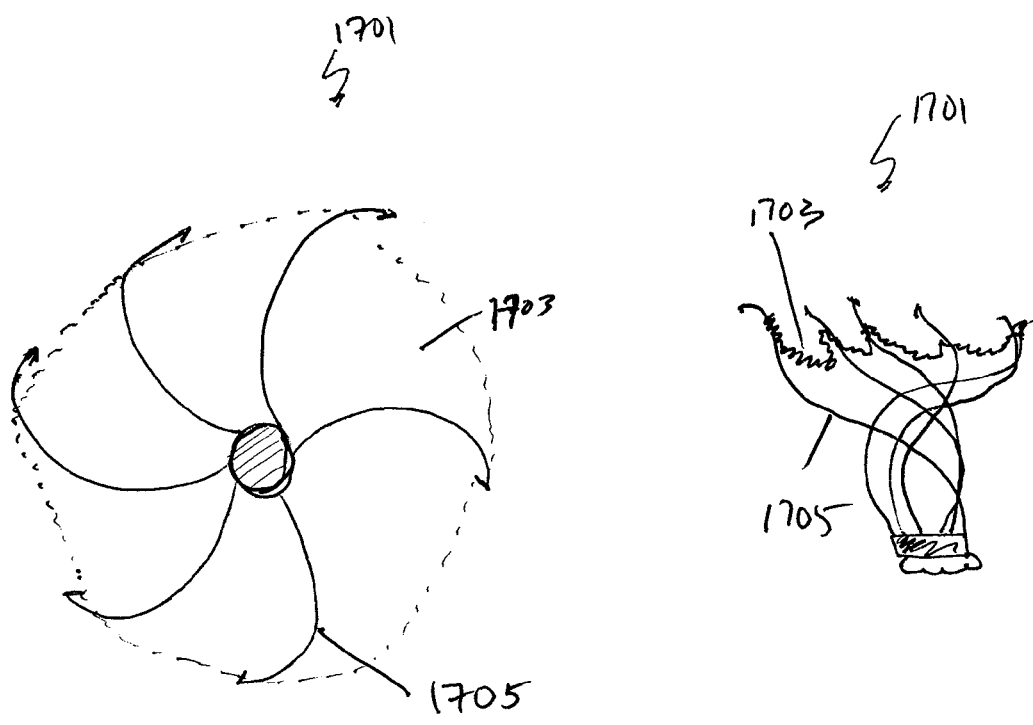
Fig. 17A
Fig. 17B

FIG. 19A
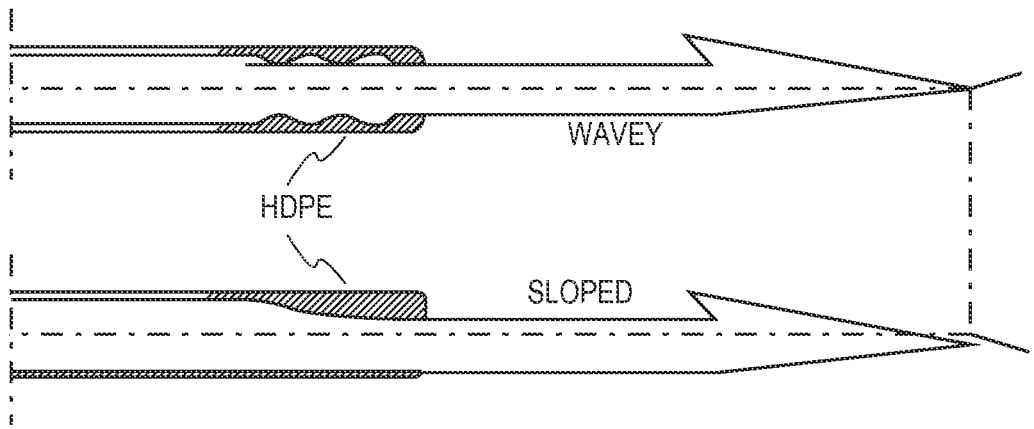
FIG. 19B
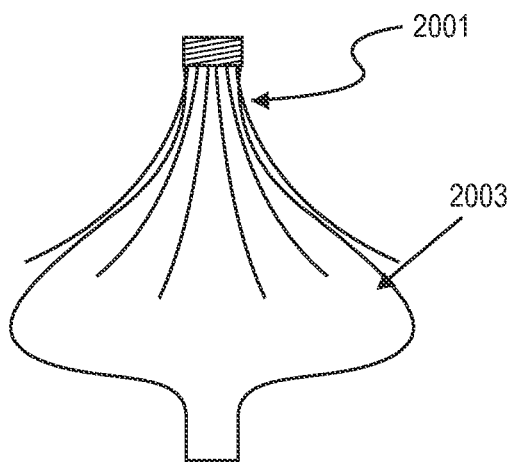
FIG. 20

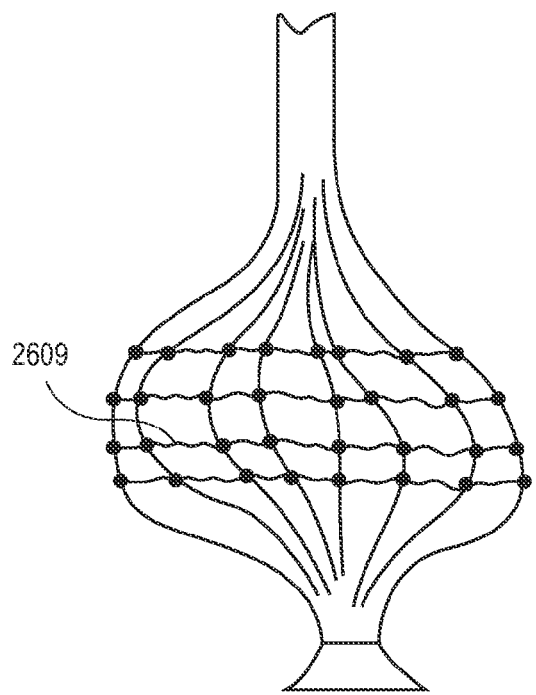
FIG. 26C
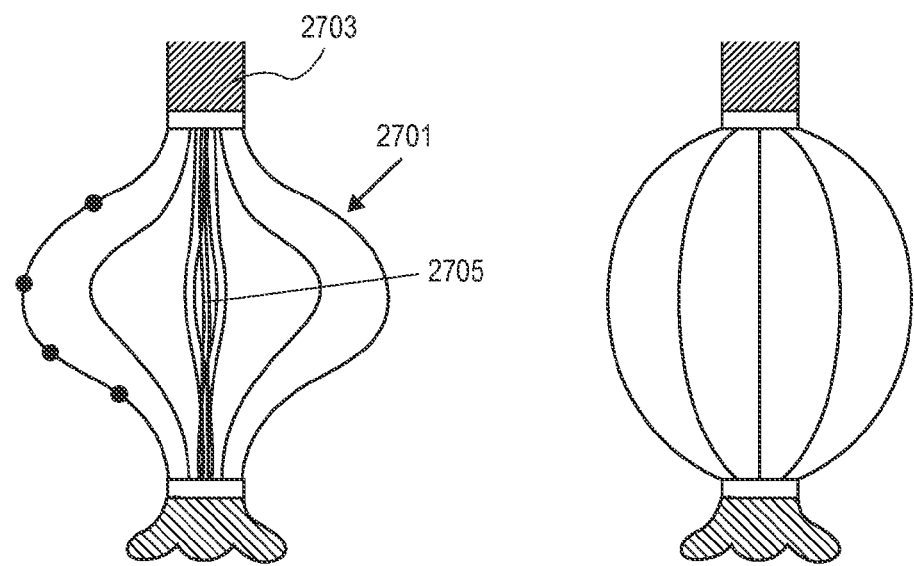
FIG. 27  FIG. 28

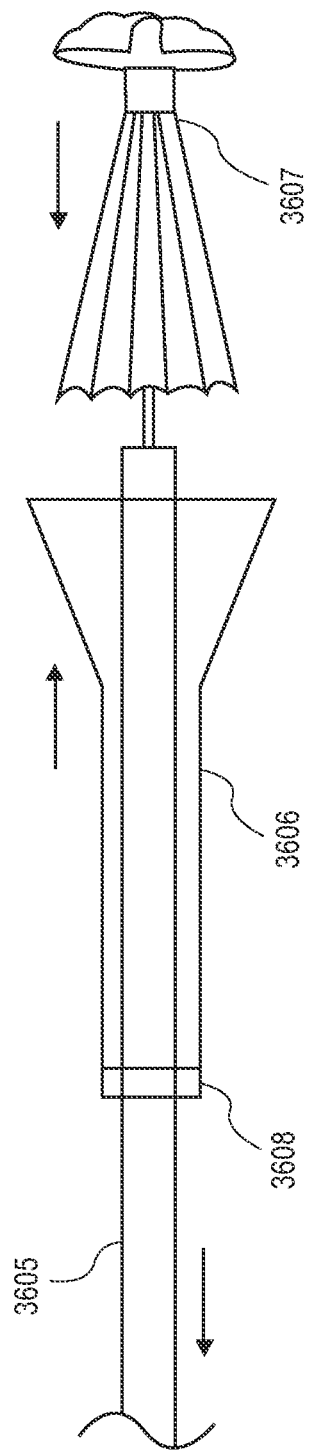
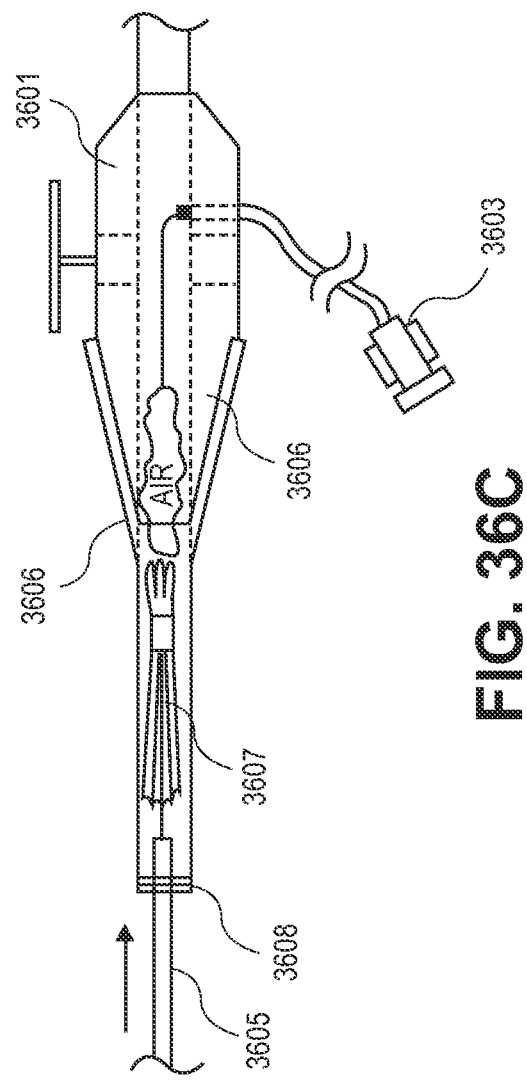
FIG. 36B
FIG. 36C

VENTRICULAR VOLUME REDUCTION

CROSS REFERENCE TO RELATED APPLICATIONS

This application claims priority to U.S. Provisional Patent Application Ser. No. 61/255,018, filed on Oct. 26, 2009, titled "VENTRICULAR VOLUME REDUCTION," which is herein incorporated by reference in its entirety.

The devices and methods described herein may be applied to many of the devices and systems described in any of the references listed below. In particular, these references generally describe devices, systems, and methods for improving cardiac function and to ventricular partitioning devices in particular. Thus, the following patents/patent applications are herein incorporated by reference in their entirety: U.S. patent application Ser. No. 09/635,511, titled "DEVICE AND METHOD FOR TREATMENT OF HOLLOW ORGANS," filed on Aug. 9, 2000; U.S. patent application Ser. No. 10/212,032, titled "METHOD FOR IMPROVING CARDIAC FUNCTION," filed on Aug. 1, 2002; U.S. patent application Ser. No. 10/212,033, titled "DEVICE FOR IMPROVING CARDIAC FUNCTION," filed on Aug. 1, 2002; U.S. patent application Ser. No. 10/302,269, titled "DEVICE WITH A POROUS MEMBRANE FOR IMPROVING CARDIAC FUNCTION," filed on Nov. 22, 2002; U.S. patent application Ser. No. 10/302,272, titled "METHOD OF IMPROVING CARDIAC FUNCTION USING A POROUS MEMBRANE," filed on Nov. 22, 2002; U.S. patent application Ser. No. 10/382,962, titled "METHOD FOR IMPROVING CARDIAC FUNCTION," filed on Mar. 6, 2003; U.S. patent application Ser. No. 10/436,959, titled "SYSTEM FOR IMPROVING CARDIAC FUNCTION," filed on May 12, 2003; U.S. patent application Ser. No. 10/754,182, titled "VENTRICULAR PARTITIONING DEVICE," filed on Jan. 9, 2004; U.S. patent application Ser. No. 10/791,916, titled "INFLATABLE VENTRICULAR PARTITIONING DEVICE," filed on Mar. 3, 2004; U.S. patent application Ser. No. 10/913,608, titled "VENTRICULAR PARTITIONING DEVICE," filed on Aug. 5, 2004; U.S. patent application Ser. No. 11/151,156, titled "MULTIPLE PARTITIONING DEVICES FOR HEART TREATMENT," filed on Jun. 10, 2005; U.S. patent application Ser. No. 11/151,164, titled "PERIPHERAL SEAL FOR A VENTRICULAR PARTITIONING DEVICE," filed on Jun. 10, 2005; U.S. patent application Ser. No. 11/199,633, titled "METHOD FOR TREATING MYOCARDIAL RUPTURE," filed on May 9, 2005; U.S. patent application Ser. No. 11/640,469, titled "CARDIAC DEVICE AND METHODS OF USE THEREOF," filed on Dec. 14, 2006; U.S. patent application Ser. No. 11/800,998, titled "SYSTEM FOR IMPROVING CARDIAC FUNCTION," filed on May 7, 2007; U.S. patent application Ser. No. 11/801,075, titled "SYSTEM FOR IMPROVING CARDIAC FUNCTION," filed on May 7, 2007; U.S. patent application Ser. No. 11/860,438, titled "LAMINAR VENTRICULAR PARTITIONING DEVICE," filed on Sep. 24, 2007; U.S. patent application Ser. No. 12/125,015, titled "VENTRICULAR PARTITIONING DEVICE," filed on May 21, 2008; U.S. patent application Ser. No. 12/129,443, titled "THERAPEUTIC METHODS AND DEVICES FOLLOWING MYOCARDIAL INFARCTION," filed on May 29, 2008; U.S. patent application Ser. No. 12/181,282, titled "INFLATABLE VENTRICULAR PARTITIONING DEVICE," filed on Jul. 28, 2008; U.S. patent application Ser. No. 12/198,010, titled "RETRIEVABLE DEVICES FOR IMPROVING CARDIAC FUNCTION," filed on Aug. 25, 2008; U.S. patent application Ser. No. 12/198,022, titled "RETRIEVABLE CARDIAC DEVICES," filed on Aug. 25, 2008; and U.S. patent application Ser. No. 12/268,346, titled "SYSTEM FOR IMPROVING CARDIAC FUNCTION," filed on Nov. 10, 2008.

FIELD OF THE INVENTION

The present invention relates generally to medical/surgical devices and methods pertaining to treating heart disease, particularly heart failure. More specifically, the inventions described herein relate to devices and methods for reducing ventricular volume.

BACKGROUND OF THE INVENTION

Described herein are devices, systems, and methods for improving cardiac function, and for reducing ventricular volume. Many of the devices and systems described herein reduce ventricular volume by partition the ventricle into productive and non-productive portions (e.g., by partially occluding a small portion of the ventricle).

Annually, heart failure leads to millions of hospital visits internationally. Heart failure (including congestive heart failure) is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischemia may, for example, cause a portion of a myocardium of the heart to lose its ability to contract. Prolonged ischaemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, distilling pressures increase, which stretches the ventricular chamber prior to contraction and greatly increases the pressure in the heart. In response, the heart tissue reforms to accommodate the chronically increased filling pressures, further increasing the work that the now comprised myocardium must perform.

Drug therapy typically treats the symptoms of the disease and may slow the progression of the disease, but it cannot cure the disease. One of the only permanent treatments for heart disease is heart transplantation, but heart transplant procedures are very risky, extremely invasive and expensive and are performed on a small percentage of patients. Many patient's do not qualify for heart transplant for failure to meet any one of a number of qualifying criteria, and, furthermore, there are not enough hearts available for transplant to meet the needs of heart failure patients who do qualify.

Substantial effort has been made to find alternative treatments for heart failure. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to the most severe class of patients and, accordingly, is not an option for most patients facing ineffective drug treatment. Finally, if the procedure fails, emergency heart transplant is the only presently available option.

Ventricular partitioning devices offer a solution for treating heart failure. Described herein are ventricular volume reduction device that may also act as ventricular partitioning devices. These devices generally function to partition a patient's ventricle into a productive region and a non-productive region. For such devices to function properly, they are positioned in a specific location within the patient's heart chamber. Delivery of a partitioning device may be made complicated by the anatomy of a patient and by aspects or characteristics of the delivery device or partitioning device itself. Thus, it would be beneficial to provide devices, systems and methods for delivering and deploying a partitioning device in a patient's ventricle.

Described herein are ventricular volume reduction devices and methods that may be implanted to reduce the volume of the ventricle in a safe and controlled manner.

SUMMARY OF THE INVENTION

Described herein are devices and systems including implants (which may be removable) and methods of using them for reducing ventricular volume. The implants described herein are cardiac implants that may be inserted into a patient's heart, particularly the left ventricle. The implant may support the heart wall, or may be secured to the heart wall. In some variations the implant is a ventricular partitioning device for partitioning the ventricle into productive and non-productive regions.

The ventricular volume reduction devices described herein may include a partitioning member (e.g., a membrane) and a frame for securing the membrane across the ventricle and/or for securing the device in the ventricle. In some variations the frame includes a plurality of individual (or connected) struts that are flexible and may collapse (for delivery) and expand (for securing in the ventricle). The struts may allow the device to flex/move in response to the motion of the heart.

In some variations, the device includes a partitioning member such as a membrane that is configured to span a mid- to lower-portion of a ventricle and to occlude a region of the ventricle (e.g., the apical region). Such devices may be adjustable (before, during or after implantation/insertion into the ventricle) to adjust the "height" of the membrane (e.g., the distance from the apex), and thereby adjust the remaining active volume in the ventricle. For example, in some variations the portion of the frame connected to the membrane may be adjusted to increase the distance from the partitioning member (e.g. membrane) and the base (e.g., foot or apical region) of the implant.

In some variations the device is configured so that the implant acts to assist with the pumping of the ventricle. For example, the device may include a contractible member (e.g., an inflatable member or balloon) that is in contact with the partitioning member to move it in a coordinated fashion with the motion of the heart walls, thereby assisting with the pumping of the ventricle. For example a balloon located in the region "behind" the implant (e.g., in the non-functional portion cut off by the partitioning member) may be cyclically inflated/deflated to assist with pumping. In other variations the balloon contacts the wall of the ventricle in this lower region, and translates the wall motion into motion of the partitioning member, to help with pumping.

In some variations the partitioning member is a membrane, as mentioned. This partitioning member may be configured so that it expands from a collapsed configuration to an expanded (ventricle-spanning) configuration. The ventricle-spanning configuration may be further adapted so that the surface is substantially smooth or free of irregularities. Such smooth surfaces may be preferable, since they may offer a lower risk of clot formation, for example, or for fluid dynamics considerations (e.g., decreasing turbulent flow). In some variations the partitioning membrane is formed of a plurality of overlapping members (e.g., leaves, etc.) that form the partitioning surface facing the active portion of the heart. For example, the parachute and fame may be constructed by cutting metal members (e.g., Nitinol) or relatively stiff, hard plastic members that may fan open or closed to expand/contract. In some variations, the membrane is formed of a relatively hard/stiff material (e.g., metal, thermoplastic, etc.) that is configured with hinged joints so that it may be collapsed for delivery and expanded once positioned. For example, the membrane may be formed of a relatively stiff material that folds along pre-determined edges. In other variations the partitioning member is a membrane that is secured to a frame (e.g., struts forming a membrane—supporting frame) only at the peripheral edge region of the partitioning member (e.g., membrane). This may allow the membrane to be held taut across the surface, rather than having the membrane to be anchored or secured more apically/distally relative to the rest of the implant.

In some variations the frame of the implant comprises a decoupled configuration including a partitioning member supporting frame and an anchoring frame. The anchoring frame and the membrane-supporting frame may comprise different (though connected) struts that are configured to expand from a delivery configuration into a deployed configuration. The struts may be formed or one or more shape memory alloy materials. In some variations, one or more of the struts forming the frame is a spiral strut, which changes shape in more than one plane. In some variations the struts forming the implant overlap in the center region (e.g., in the axial middle region of the implant). The overlapping region may further support the partitioning member, reducing the volume. In some variations the struts forming the frame include inner and outer strut regions (e.g., the struts double back on themselves). The inner and outer struts may be differentially connected to the partitioning member and configured to contact tissue.

Also described herein are implants including frames having one or more bridge struts. The bridge struts may couple adjacent struts to enhance the strength and/or durability of the struts once the device is in the implanted configuration.

"Tall" implants including a membrane and a support or strut region are also described. In such variations the struts (which may be arranged as spiral struts, described above, extend up from a foot or apical region to bend of nearly 90° (e.g., between 60° and 90°, between about 70° and 90°, between about 80° and 90°, etc.) the top region of the implant, to which the membrane is connected, may be substantially flat (formed of the upper half of the struts, to minimize the ventricular volume.

A ventricular volume reducing device may also include one or more struts that are hinged or otherwise configured to open/collapse the partitioning element (e.g., membrane). Thus, the device may include a frame that converts from an extended configuration (collapsed) in which distal and proximal strut regions are in the same plane, connected at respective distal and proximal ends, and arranged end-to-end. For example, in an umbrella-frame configuration, the struts may be deployed from this small-cross-sectional configuration by collapsing downward along the hinge region near the respective distal and proximal ends of the struts, thereby changing the angle between the distal and proximal struts from 180° to less than 90° (e.g., less than 45°, or between 10° and 45°, etc.). Converting the implant in this manner may arrange the partitioning member across the diameter of the ventricle to partition it, as mentioned above. The hinge region between the proximal and distal struts may also include one or more anchoring features (e.g., hooks, barbs, etc.).

Another variation of a ventricular volume reducing device include a frame comprising struts that expand from a common apex, wherein two struts are substantially parallel to each other. This may allow the membrane to be folded between the struts so that as it expands, membrane maybe held taught, preventing the formation of significant 'pleat' regions. Thus, the frame may include one or more struts that help manage the membrane. In this example, the membrane may be held taut on the face of the membrane facing the active ventricle region. This variation may be referred to as "scissor struts."

Also described herein are ventricular volume reduction devices which do not include a "foot" region, but mechanically expand within the ventricle to contact the walls of the ventricle only from the sides (rather than the apex). For example, such a footless configuration may include an upper and lower frame that both include membranes and have radially extending struts that all terminate in anchors.

Although many of the variations described herein include struts formed of a flexible material such as a metal (e.g., Nitinol, stainless steel, etc.) or a plastic (e.g., thermoplastic), the struts may, in some variations, be inflatable struts. Inflatable struts may be formed of laminated layers (sealed) of material (including the membrane material) that are inflated with a fluid (e.g., gas, liquid, etc.) or hardenable resin/epoxy upon insertion into the ventricle.

In some variations the ventricular partitioning device may be configured to include one or more visualizable (e.g., under fluoroscopy, ultrasound, etc.) element. For example, the device may include a single strut that is configured to be visualized (e.g., coated with or formed by a radioopaque material). Such variations may be particularly useful for asymmetric devices. In some variations more than one strut may be marked for visualization. In some variations, the device may be marked with an oriented marker (e.g., an asymmetric shape) allowing better resolution of the three-dimensional orientation of the device even in a 2D fluoroscopic image. In some variations the device may be marked with words, phrases, images, icons, or the like.

A ventricular partitioning device may also include self-tapping struts that are configured to expand and rotate or otherwise drive themselves into the ventricular wall upon implantation. In one variation the implant includes spiral-cut or formed struts that expand towards the wall of the ventricle while driving the foot region (or lower region) of the implant towards the apex of the heart.

Any of the strut variations described herein may be formed of two or more layers of material (e.g., formed by cutting two abutting layers of thin Nitinol material, such as two concentrically arranged tubes). The thin material may be cut to form two (or more) layers of struts. These struts may have different thicknesses. Processing may be improved by providing multiple relatively thin layers of near-overlapping material to form the struts, rather than a single thick layer (having an equivalent thickness to the multiple thin layers).

In variations of the ventricular volume reducing devices described herein including a membrane (and particularly a flexible membrane), the membrane may be advantageously secured to the frame (e.g., struts) in various ways. For example, in some variations the membrane is secured to the frame by including eyelet regions (e.g., pre-formed concavities) on the struts to provide a bonding region. Each strut may include one or more such regions.

In some variations, the membrane of the implant may be formed directly onto the struts by dip coating. For example, the frame (in an expanded configuration) may be applied to a polished mandrel and used to dip coat into a polymer solution that will harden on the mandrel, and be attached to the frame. Multiple dip coatings (with or without the mandrel) may be performed.

The membrane may be formed of different materials, or may have different regions that have different or complementary properties. For example, the implant may include an outer membrane formed of a membrane (e.g., ePTFE) that is optimized for tissue in-growth, while the inner membrane (facing the non-functional portion of the ventricle when implanted) may be optimized for hydraulic load (e.g., creep resistance).

In some variations the membrane may encapsulate or surround portions of the device. For example, the edge of the membrane may be laminated back on itself to enclose or partially enclose a support element, a collapse element or the like (e.g., a string or suture). In some variations the different radial sections of the membrane may be separated by spacers to aid deployment. For example, the edge or rim region may include a metal or elastic polymer that helps the membrane fully deploy during operation. This spacer may also help seal the membrane to the wall of the ventricle, and may prevent the membrane from sticking to itself when the device is expanded from the collapsed configuration.

Generally, the membrane may be formed or secured to the implant frame (or struts) in a pre-loaded configuration. For example, although the implant frame may be configured to expand to a fully expanded configuration (having a maximum diameter) of 100%, the membrane may be attached when the frame (or individual struts of the frame) are only partially expanded (e.g., 90%, 85%, 80%, 75%, 70%, etc. expanded). This may also be referred to as preloading the frame. Since the membrane is slightly elastic, the load (expansion force) applied by the frame when implanted into the ventricle may allow it to expand slightly. In this manner, the membrane may be laminated in nearly the size (or slightly larger than the size) of the implanted device.

In variations of the devices including a foot region that is configured to contact the wall (e.g., apical region) of the ventricle, the tissue-contacting regions may be configured of a softer polymer (e.g., having a lower durometer) than the rest of the foot and/or hub. In some variations the foot region may be inverted or invertable, so that it does not prevent the frame or a portion of the frame from getting as close as possible to the wall of the ventricle.

In some variations, the device ventricular volume reduction device includes one or more conical, self-expanding structures configured to be inserted into the apex of the ventricle to reduce the volume of the ventricle. This variation of the implant may be inflatable. This variation, may or may not include an additional partitioning membrane, such as a membrane spanning the top portion of the device (e.g., facing away from the apex of the ventricle when inserted). This variation may also not include a separate frame as described in many of the device variations above.

Also described herein are stacking devices that may be used either to reduce ventricular volume, or to protect from myocardial infarction.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

FIGS. 13E and 13F show detail of the hinge region between different strut domains.

FIG. 16 shows a variation of an inflatable ventricular volume-reduction implant.

FIG. 17A and 17B shown a top view and a schematic cross-section through one variation of a ventricular volume-reduction implant having self-tapping struts.

FIGS. 19A and 19B illustrate regions of struts to which a partitioning element (e.g., membrane) may be secured.

FIG. 20 illustrates a mandrel for dip-coating an implant.

FIG. 26B illustrates the sizer of FIG. 26A inserted and deployed within the ventricle.

FIG. 26C shows another variation of the sizer of FIG. 26A.

FIGS. 27 and 28 show additional sizer variations.

FIGS. 36A-36C illustrate a system for loading an implant into a guide catheter for insertion.

DETAILED DESCRIPTION

Figure 1A:
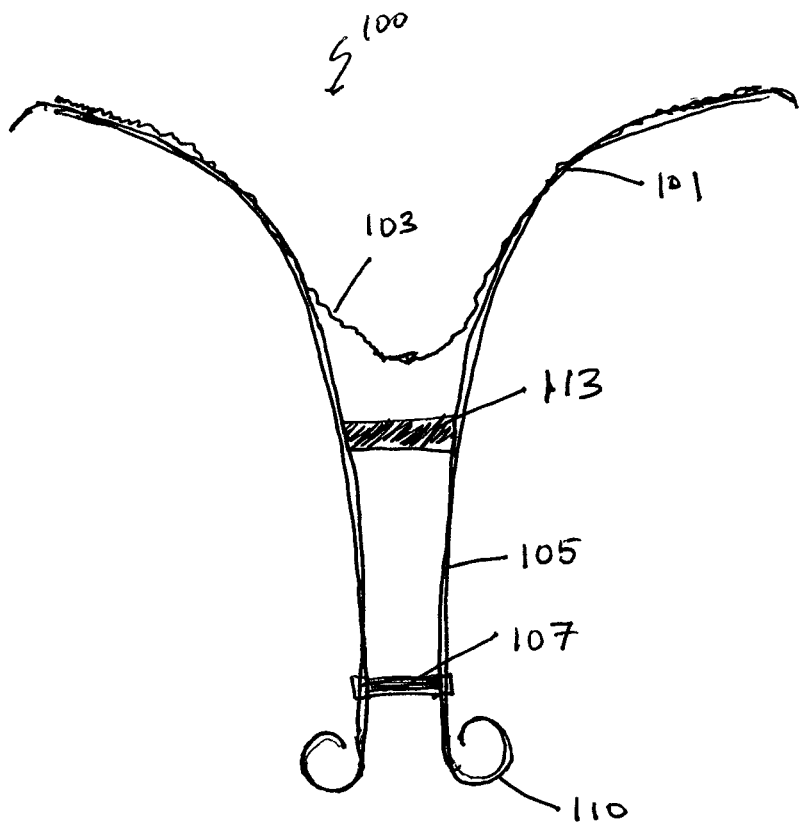
FIGS. 1A and 1B show one variation of an adjustable-height implant for reducing ventricular volume as described herein, in a tall (FIG. 1A) and short (FIG. 1B) configuration.

In general, described herein are implant for insertion into a patient's ventricle (e.g., left ventricle) to reduce ventricular volume by partitioning the ventricle into a productive and a non-productive portion. In some variations of these implants, a partitioning element, which may be a surface, extends at least partially across the diameter of the ventricle to partition the ventricle and thereby reduce the volume. In some variations the partitioning element is a membrane, which may be flexible. One or more supports may be used to support the membrane. An implant may also include one or more struts that can expand and collapse as necessary, and may span the diameter of the ventricle to position and/or anchor the partitioning element across the ventricle. In general, these implants may be delivered in a low-profile collapsed configuration and expanded in the ventricle to reduce the volume of the ventricle.

For example, in some variations the implants include a partitioning element, and plurality of struts that may be expanded from a collapsed configuration into an expanded configuration in which the partitioning element (e.g., membrane) is extended and anchored across the ventricle to reduce ventricular volume. The implant may also include a hub (e.g., a central hub) from which the plurality of struts extends. In some variations the implant include a foot extending from the hub of the implant; the foot region and the hub may be separated by a body region. The body region therefore set the "height" of the implant from the foot to the partitioning element. In general, the foot region may be an atraumatic foot that is configured to rest against the surface of the heart (e.g., the ventricle). In some variations the foot region may act as an anchor that penetrates the heart and helps secure the implant in position.

In general, the implant may be anchored or otherwise secured across the ventricle to reduce ventricular volume. Thus, the implant may include one or more (or an array of) anchors for securing the implant in position within the ventricle, preferably within the apical region of the ventricle. In some variations the outer edge or edges of the partitioning element include one or more tissue penetrating elements that help anchor the implant in position. For example, the end of the struts supporting a partitioning element (e.g., membrane) may be configured as tissue-penetrating barbs, hooks, or the like. These ends regions may penetrate the ventricular wall (even just slightly) to secure the implant within the ventricle.

In some variations the edge of the partitioning element is configured to seal against the wall of the ventricle. A seal may be formed with the wall by any appropriate means, including adhesive means (using a biocompatible adhesive), inflatable means, swellable means, pressure-applying means, or the like.

It may be desirable to adjust or control the size of the region the ventricle portioned, and therefore the amount of volume reduction in the ventricle, by controlling the size and dimension of the implant. For example, in the variations of implants illustrated in FIGS. 1A-2, the height of the implant may be adjusted. The height of the implant may refer to the height of the implant from an (option) foot region to the surface of the partitioning element crossing the ventricle volume.

For example, FIG. 1A shows a side section though one variation of an adjustable-height ventricular volume reduction implant. In FIG. 1A, the implant 100 is shown in a "tall" configuration. The implant 100 includes a plurality of struts 101 (two of which are visible in this cross-sectional schematic) that may be arranged radially extending from the longitudinal midline of the device. FIG. 1A shows the implant 100 in an expanded configuration, in which the partitioning element (membrane 103) is extended and configured to partition off a portion of the ventricular volume when the implant has been delivered within the ventricle. The implant includes a plurality of distal struts 105 that are contiguous with the support struts 101 supporting the membrane 103. The distal struts may form a stem region. An atraumatic footer region 110 is formed by the distal ends of the distal struts 105. In addition, a sliding collar 107 is included, and is shown locked (or otherwise secured) near the distal end of the implant, before the foot region 110. A hub 113 to which the struts are connected is located proximally, before the expanded support struts 101.

Figure 1B:
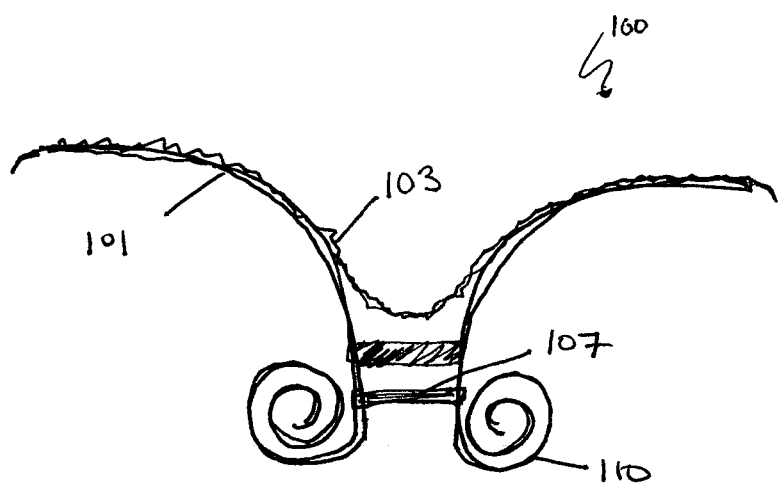

The height of this implant may be adjusted by sliding the collar 107 towards the proximal end, as shown in FIG. 1B. In this example, as the collar is adjusted, the distal struts maybe foreshortened distal to the collar by curling up, to form the foot region 110. Thus, in this example an additional foot may not be needed, although it could be optimally included. In addition, the implant may include a lock for locking the collar 107 at a desired height.

Figure 2:
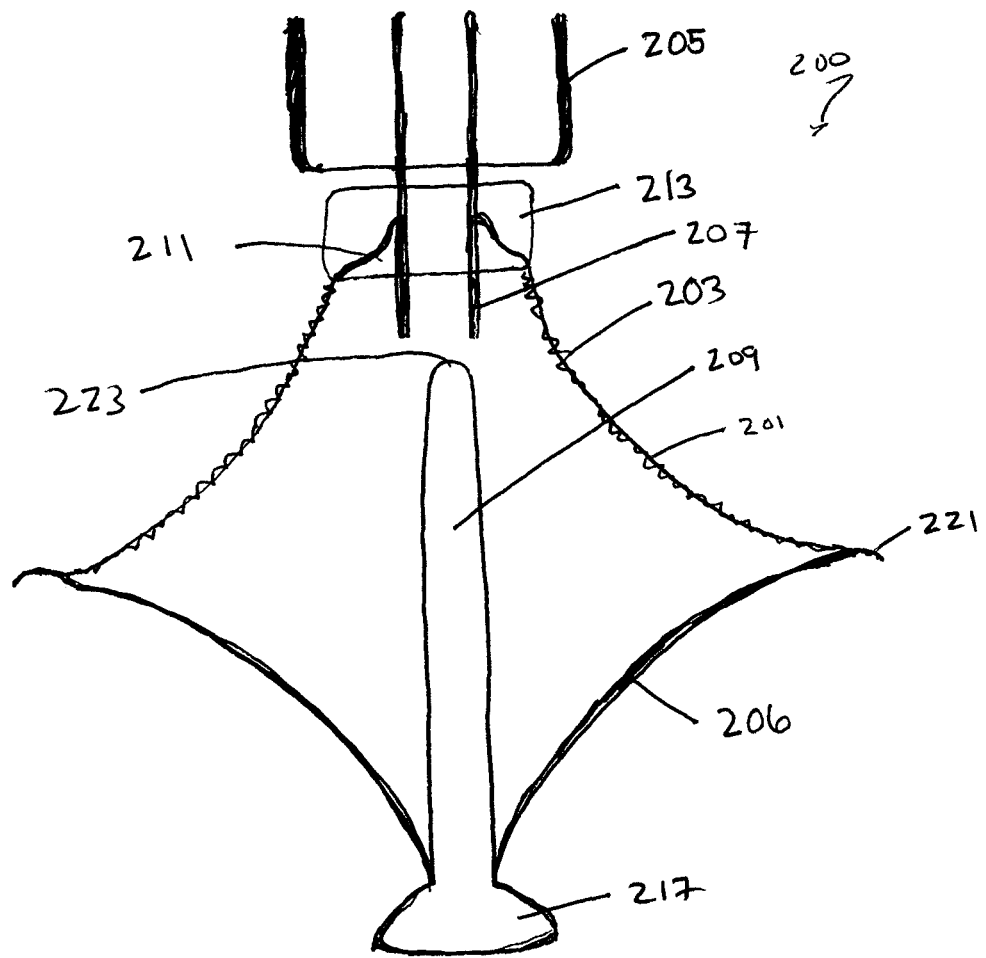
FIG. 2 shows another variation of an expandable implant for reducing ventricular volume that is retractable and height-adjustable.

FIG. 2 shows another side schematic view of an implant 200 that is height-adjustable. In this variation, the implant includes a membrane-type partitioning element 203 that is secured to a plurality of struts 201. The implant may be mechanically engaged with a ventricular wall (including by anchoring by one or more anchors 221). A delivery device for delivering the implant in the collapsed configuration (not shown) may also be configured for adjusting the height of the implant. For example, the delivery device may include a pusher tube 205 that includes a surface to push against (and collapse) the collar element 213, which is similar to the hubs described elsewhere. This collar may be pushed over the stud or post 209. The applicator/delivery device also includes a lock release (shown as a tube 207 in FIG. 2). This lock release prevents the collar, which may include locking mechanism (e.g., locking tabs 211) from securing to the stud/post 209 until the lock release tube is removed. Removing the lock release tube and allowing the locking tabs to engage the post may secure the device at a desired height. The collar 213 may be formed as a portion of the frame (including the struts). As in any of the variations described herein, the struts of the implant may be formed of any appropriate material, including Nitinol and stainless steel.

The upper 201 (and in some variations lower) struts may be coupled to the membrane 203 forming the partitioning element. For example, the membrane may be formed of ePTFE or other flexible material; in other variation the membrane is a mesh or webbing. In some variations the membranes used herein are impermeable. In still other variations, the partitioning element is formed of stiff and/or rigid materials.

The post/stud element 209 may include a lumen or passage 223 through which one or more components of the delivery device may engage. The outer surface of the post/stud element may also be configured to allow secure locking of the collar by the locking mechanism. For example, the outer surface of the post may include notches, ridges, holes, or the like for the locking mechanism to engage. The implant may also optionally include a foot element 217 at the distal end.

Figure 3A:
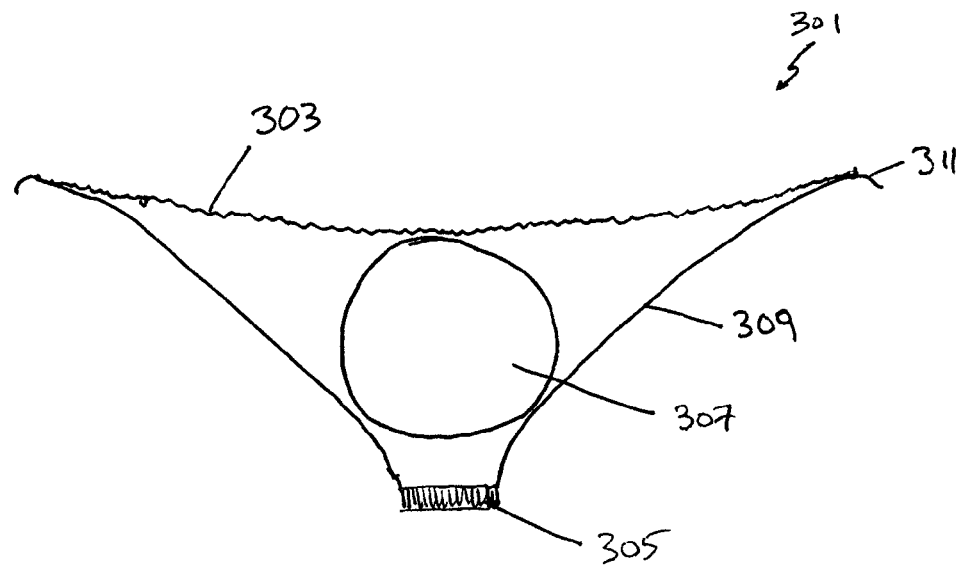
FIGS. 3A-3C illustrate one variation of an implant for reducing ventricular volume that is configured as a pumping-assist implant.

Any of the variations of the implants described herein may also be configured as pumping assist implants, which (in addition to reducing ventricular volume) may actively or passively aid in ventricular pumping. For example, FIG. 3A illustrates one variation of an implant configured as a pumping assist device. In this variation, the implant 301 includes a membrane 303 that is coupled to a frame of struts 309 attached at a central hub 305. A pumping assistance element (shown in this example as balloon 307) is positioned behind the membrane 303 to actively help the pumping of blood in/out of the ventricle.

In this variation, the pumping assistance element 307 within the assembly is captured between the frame and the positioning membrane. The balloon may be further equipped with an inflation/deflation port (not shown); the balloon port may communicate with an inflation/deflation source (e.g., outside of the ventricle) that may assist with pumping. The location of the balloon may allow the forces on the membrane to be transmitted to the frame of the device rather than the damage apical region of a patient's heart.

Figures 3B, 3C:
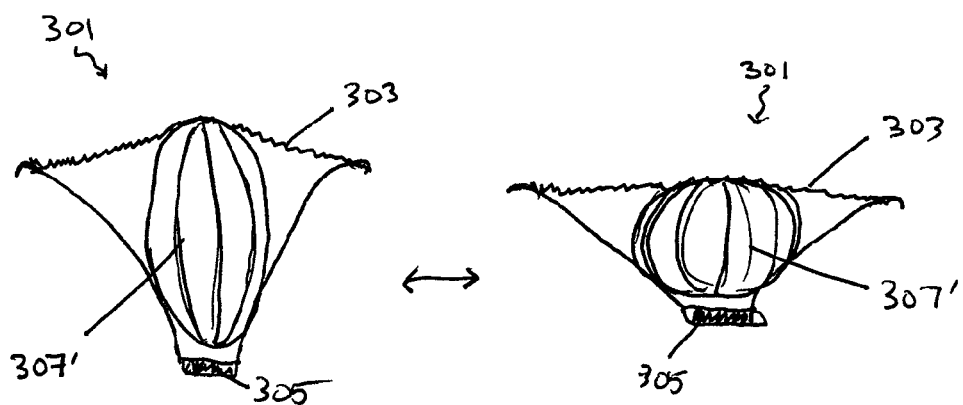

The pumping assistance element may function in two or more different modes. For example, the pumping assistance element may be actively inflated/deflated in coordination with the ventricle contraction; thus the pumping assistance element may be able to effect maximum upward deflection of the membrane, which in turn prompts enhanced ejection of the blood. In a second mode, the pumping assistance element may be let filled to a fixed volume. In this mode, the pumping action of the heart compresses the frame, and causes the membrane to deflect, passively assisting with pumping, as illustrated in FIGS. 3B and 3C. In FIG. 3B, the device is shown in a contracted configuration when secured (e.g., via anchors 311) to the ventricle wall, where the ventricle is contracted. When the ventricle expands, as shown in FIG. 3C, the membrane 303 is allowed to move towards the distal end of the device, as the balloon 307' is collapsed downward slightly. In some variations the pumping assistance element is not a balloon, but is an incompressible, elastic structure. The pumping assistance element may be toroidal, or otherwise shaped to allow a central passage therethrough, which may assist with deployment/delivery of the device. The pumping assistance device may also include a partitioning or coating to prevent tissues from adhering to the balloon.

Figures 4A, 4B:
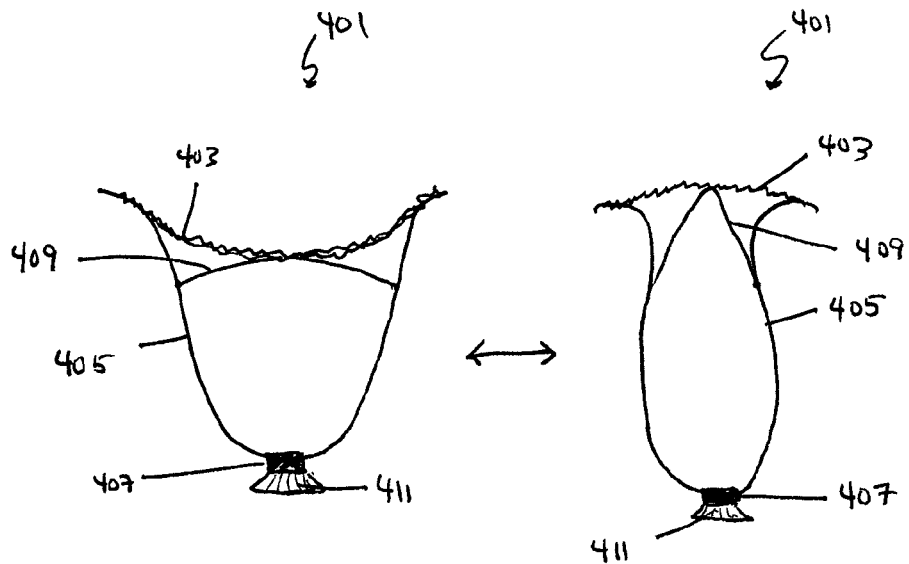
FIGS. 4A and 4B show another variation of a pumping-assist ventricular volume reducing implant.
Figures 5A, 5B:
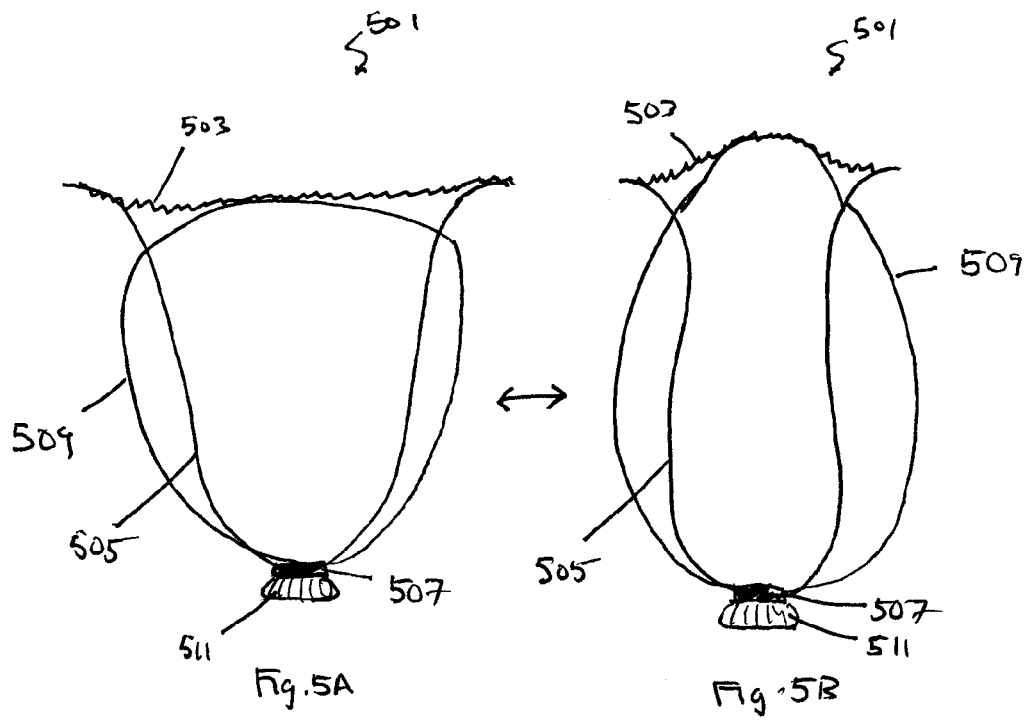
FIGS. 5A and 5B show another variation of a pumping-assist ventricular volume reducing implant.

Another variation of a pumping assistance element in an implant 401 for decreasing ventricular volume is shown in FIGS. 4A and 4B. In this example, the device includes a strut 409 that acts as a bridge element between the struts 405 (or supports) forming the frame. The bridge element 409 may also help support the membrane 403. The implant may also include a hub 407 and a foot 411. In this example, during diastole, shown in FIG. 4B, the membrane is supported by the bridge member 509, but allowed to collapse slightly; during systole, shown in FIG. 4C, the membrane is still supported by the bridge member 509, but at a level much higher than it is during diastole. The reduction in volume when the implant compresses causes the membrane to bulge outward, assisting in pumping. In FIGS. 5A and 5B the special support struts 509 may also be referred to as pumping struts, and may support the membrane. A plurality of such struts may extend under the membrane.

Although the majority of the implant variations described herein include a membrane as illustrated above, which may be made from a flexible material (e.g., ePTFE or other appropriate material), in some variations it may be desirable to have the partitioning element made of a more self-supporting material. Thus, in some variations a separate support frame may not be necessary. The frame generally provides support of the partitioning element (and anchoring of the device in the ventricle). In some variations the partitioning element is made more rigid so that an addition support (e.g., from the frame) is not necessary, though it may still be included.

Figure 6A:
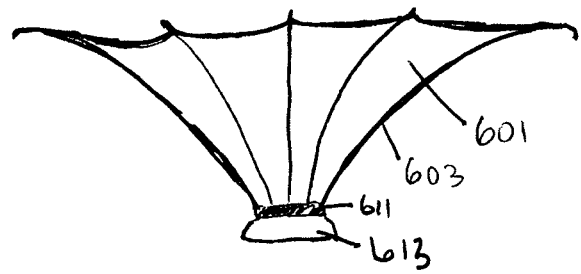
FIG. 6A shows one variation of a ventricular volume-reduction implant in cross-section through the midline of the device.
Figure 6B:
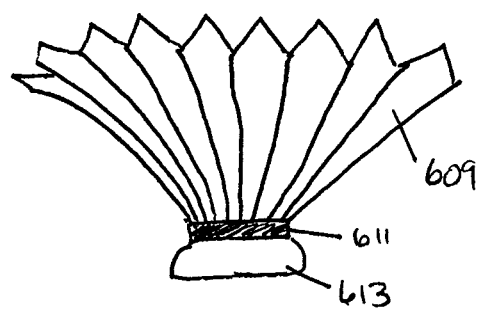
FIG. 6B shows another variation of a ventricular volume-reduction implant in cross-section.

FIG. 6A illustrates a typical flexible membrane, formed of a material such as ePTFE 601 that is supported by struts 603 which are joined to a central hub 611. An optional foot 613 is also shown. In contrast, FIG. 6B illustrates a partial side-view through an implant (sectioned through the middle) in which the partitioning element if formed by overlapping plates or wickets 609. The wickets 609 may also be referred to as leaves. The 95 mm implant shown includes multiple wickets that are formed into overlapping plates that may be fanned out to deploy from a condensed (collapsed) configuration, as shown. In FIG. 6A, the plates 609 extend from a central hub 611 and/or a foot 613.

Figure 7A:
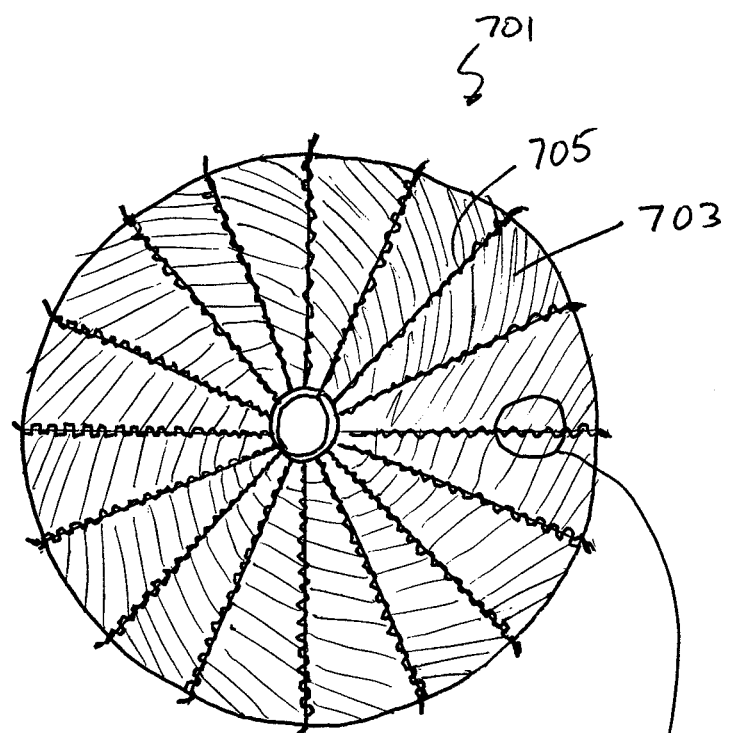
FIGS. 7A and 7B illustrate one variation of a ventricular volume-reduction implant from a top view (FIG. 7A) and a detailed view of one region of the implant (FIG. 7B).
Figure 7B:
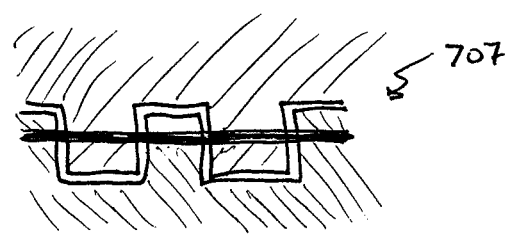

FIGS. 7A and 7B illustrate another example of an implant 701 in which the partitioning element 703 is somewhat rigid, and is formed of a series of semi-rigid plates that extend between struts 705; adjacent plates are hinged to each other along the struts, as shown in the detailed section of FIG. 7B. In this example, the joints are hinged with square joints, however other joints (triangular, sinusoidal, etc.) may also be used. In some variations the rigid or semi-rigid plates may be formed by partially or completely laminating a flexible membrane that is secured to the ribs. Self-supporting variations as described herein may be useful to avoid the problem of the implant sticking to itself prior to deployment; in particular to avoid the flexible membrane from sticking to itself or from requiring support to maintain the partition within the ventricle.

Figure 8:
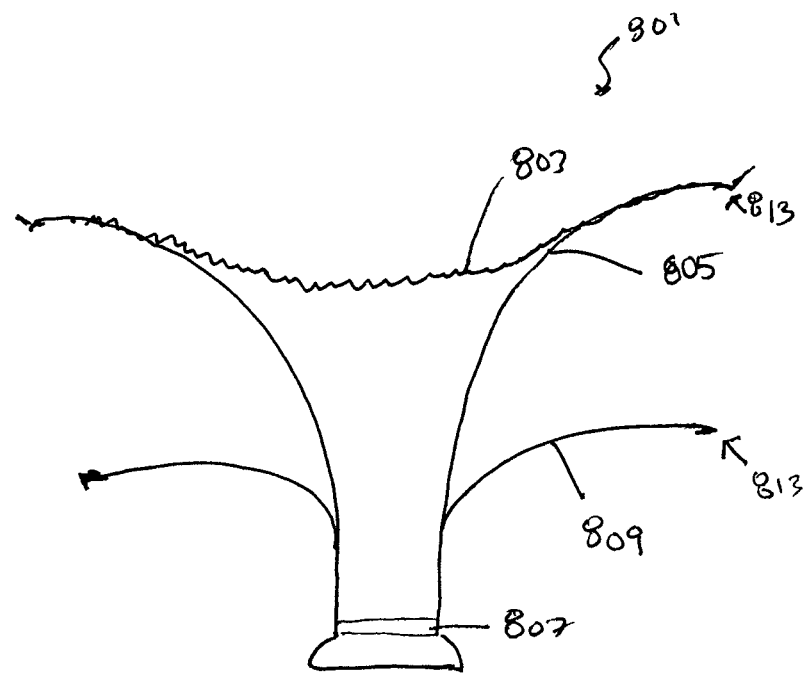
FIG. 8 shows a schematic cross-section through one variation of a ventricular volume-reduction implant.

In some variations the struts to which the partitioning member are secured are also used to anchor the implant within the ventricle. In some variations, it may also e beneficial to separate or additionally include struts that do not support the partitioning member, but that help anchor the implant. For example, FIG. 8 shows one vacation of an implant having anchoring supports that are decoupled from the partition element. In FIG. 8, the implant is similar to other implants described herein (e.g., FIG. 6A), but includes an additional set of anchoring struts 809 around the periphery of the device towards the distal end. The implant 801 otherwise includes a membrane 803 that is secured to support struts 805 (which may include additional anchors 813' at their distal ends. The struts are joined to each other at their distal ends at a central hub 807, which is connected to an (optional) foot, as shown. As with any of the struts shown herein, the anchoring struts may also include hooks, barbs, or other anchoring members at their distal ends 813.

It may also be beneficial to include one or more members for supporting the partitioning element (e.g., membrane) from within the device. For example, one or more specialized struts may be configured to assume a supporting shape beneath the membrane to help maintain the membrane in a somewhat 'flat' or more volume-reducing configuration.

Figure 9A:
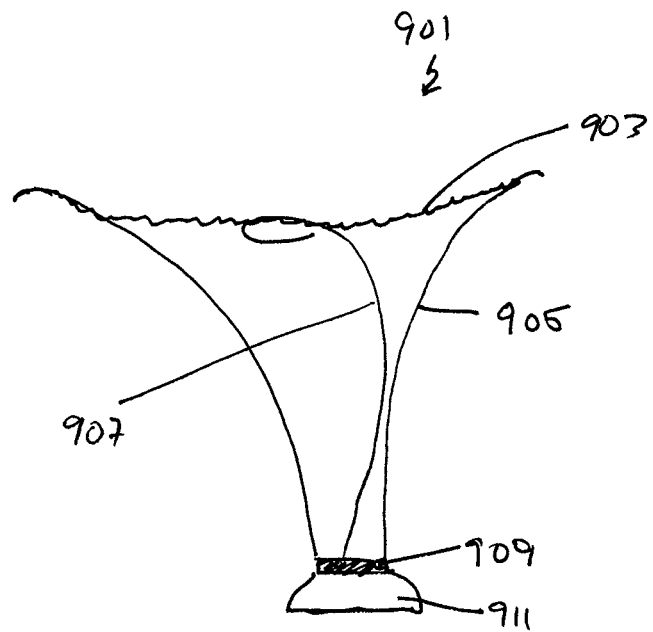
FIG. 9A shows a schematic cross-section through one variation of a ventricular volume-reduction implant.
Figure 9B:
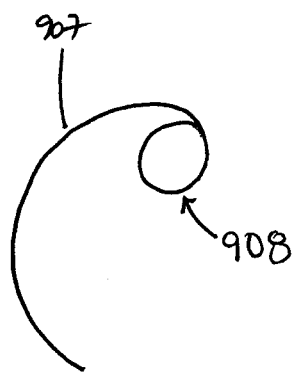
FIGS. 9B and 9C show the spiral strut of FIG. 9A from a top and side view, respectively.
Figure 9C:
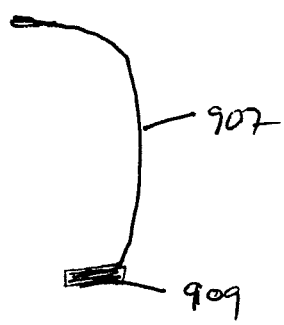

In FIG. 9A, the implant 901 is shown with a membrane 903 supported around its periphery by a plurality of struts 905. The implant also includes a central spiral strut 907 that extends around the internal region of the implant to support and underlie the membrane 903, as shown. In this example, the spiral support may allow a large region of contact (and therefore support) of the membrane. More than one support strut may be used. FIGS. 9B and 9C illustrate top and side views, respectively, of the support strut. In some variations, the support strut bends in two planes (in contrast with the other struts 905, which bend in just one plane). The spiral struts may therefore support the membrane in this variation to prevent changes in height even as the ventricle contracts.

Figure 10A:
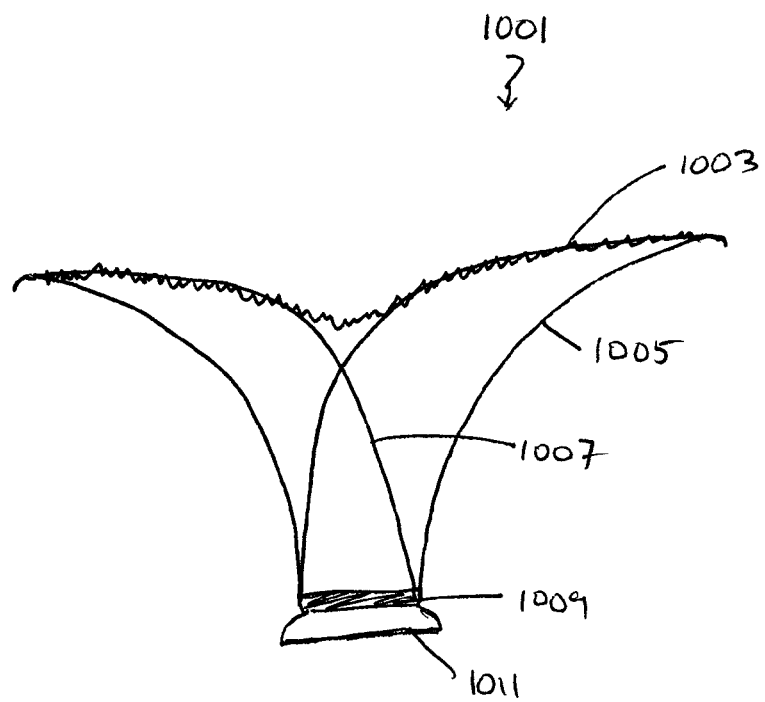
FIG. 10A shows a schematic cross-section through one variation of a ventricular volume-reduction implant having partitioning member support struts.
Figure 10B:
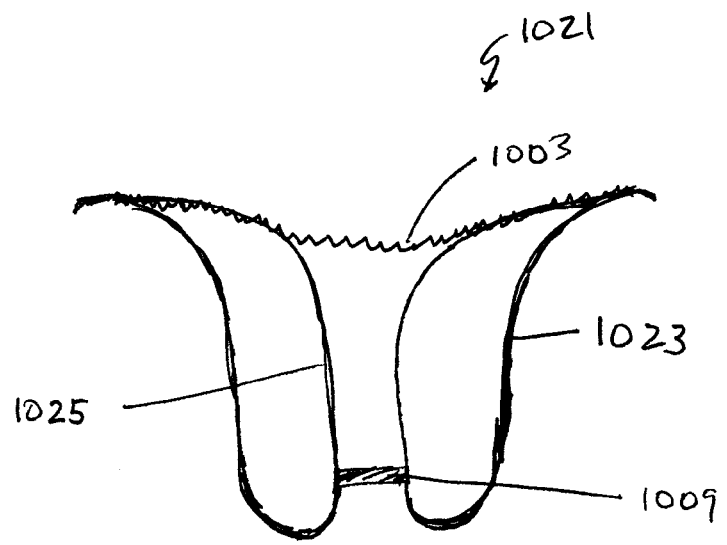
FIG. 10B shows a schematic cross-section through another variation of a ventricular volume-reduction implant having support struts.

FIGS. 10A and 10B illustrate two additional variations of implants having support struts. In FIG. 10A, the implant 1001 includes a membrane 1003 connected at its periphery by a plurality of struts 1005, and supported internally by a plurality of support struts 1007. These support struts are reverse struts 1007 which extend underneath the membrane 1003. All of the struts in this example are connected to a single hub 1009, although in some variations no single hub is used; for example, multiple hubs or strut attachment sites may be used.

In FIG. 10B, the implant 1021 also includes a plurality of support struts 1025, which are formed from the same continuous strut as the anchoring struts 1023 on the outside of the implant. In this variation the strut is bends around itself, and multiple struts are joined at a distal hub 1009. The membrane 1003 is coupled to both ends of the struts 1023, 1025. The implant may therefore have struts that cross over the midline of the device (as shown in FIG. 10A) or approach the midline (as shown in FIG. 10B) and provide support beneath the partitioning element, allowing reduction of the volume of the ventricle when the implant is deployed therein.

Figure 11A:
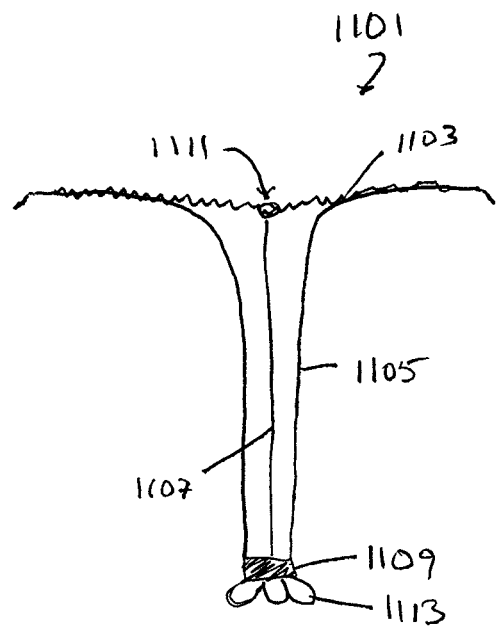
FIGS. 11A and 11B show a schematic cross-section through, and a top view of, one variation of a ventricular volume-reduction implant, respectively.
Figure 11B:
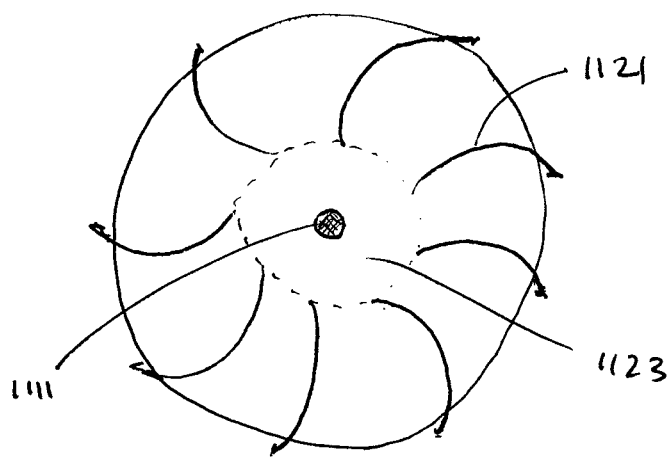

FIGS. 11A and 11B illustrate another variation of an implant with support under a majority of the partitioning element (membrane 1103). In this example the implant is a tall partitioning implant 1101 that include spiral struts 1105. These struts include a free proximal end that extends at an angle from the elongate body of the device, providing support underneath a majority of the membrane 1121. FIG. 11A shows a schematic side view through the midline of the device, while FIG. 11B shows a top view down on the partitioning element. In FIG. 11B, the dashed line indicates the different regions between supported portion 1121 and the unsupported portion 1123.

Figure 12:
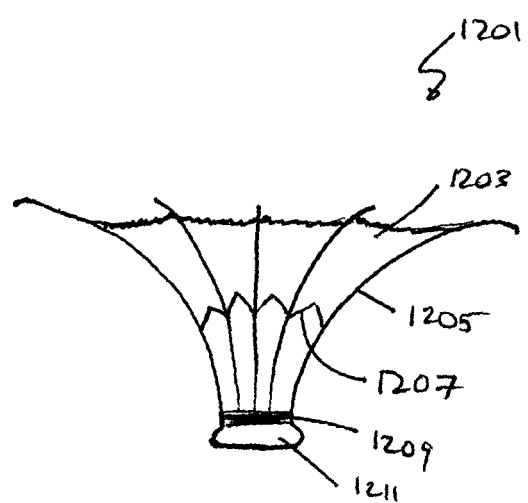
FIG. 12 shows a schematic cross-section through one variation of a ventricular volume-reduction implant having cross-struts.

In some variations of the implants described herein it may also be desirable to include one or more bridges between struts in the implant. For example, FIG. 12 illustrates one variation of an implant 1201 including a plurality of bridge struts 1207 between adjacent struts supporting the membrane 1203 and anchoring the device. By adjusting the height (e.g., along a proximal-distal axis of the implant) at which the bridge elements are placed, the relative stiffness and dynamic motion of the frame may be modified or regulated.

Figures 13A, 13B:
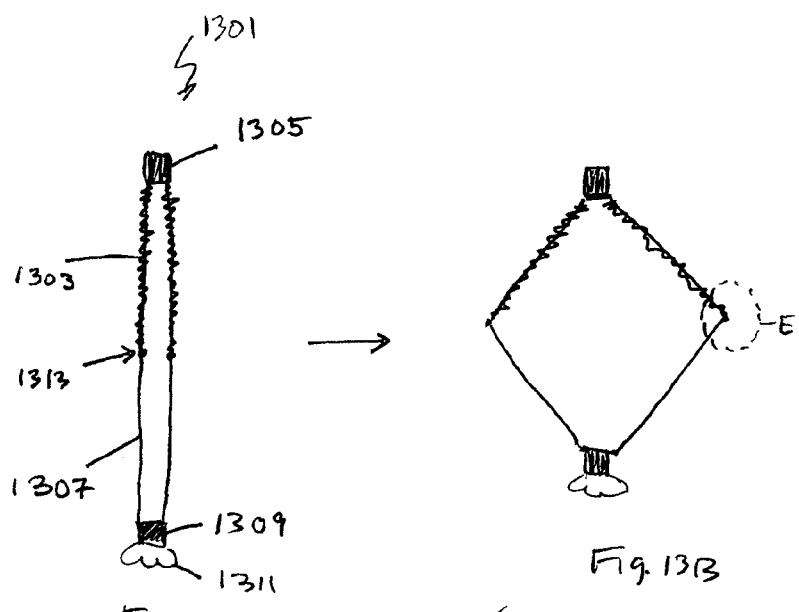
FIGS. 13A-13F illustrate one variation of a ventricular volume-reduction implant deployed form a collapsed configuration (FIG. 13A) into a deployed configuration (FIG. 13D).
Figures 13C, 13D:
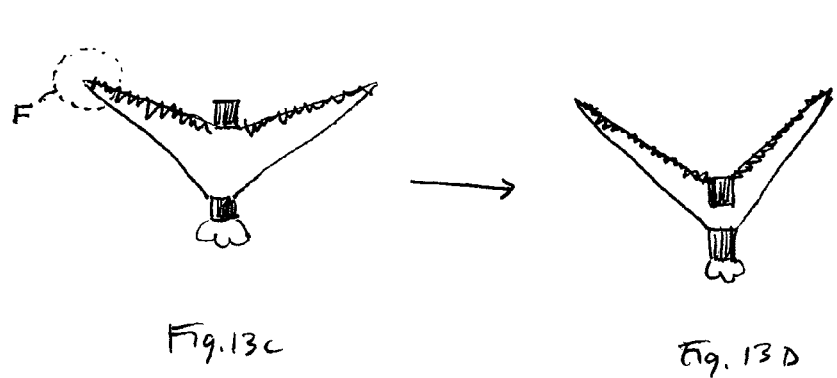
Figures 13E, 13F:
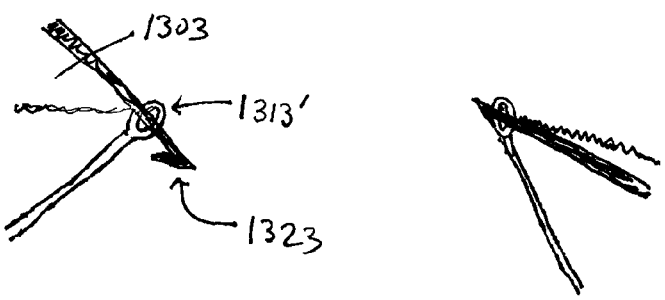

FIGS. 13A-13F illustrate one variation of an implant in which the implant expands opening similar to an umbrella. FIG. 13A shows the implant 1301 in a collapsed, or delivery configuration. The implant includes an upper region having a plurality of struts 1303 with an attached membrane. The upper region is connected at the proximal end to a proximal hub 1305, and at the distal ends to a lower region having a plurality of lower struts 1307. The lower struts are also connected at the distal end to a distal hub 1309, and the implant may include an optional foot 1311. FIGS. 13B to 13D illustrate expansion of the implant from the collapsed configuration shown in FIG. 13A to the fully deployed configuration shown in FIG. 13D. After positioning the implant within the ventricle, the upper hub 1305 may be pushed towards the lower hub 1039 until the upper frame passes (snaps past) its inflection point (FIG. 13C), which may lock the implant in the deployed configuration (FIG. 13D). Once in the deployed configuration, the implant may be locked or secured in position by connecting or securing the two hub regions relative to each other (not shown). FIGS. 13E and 13F illustrate the hinged region between the upper 1303 and lower 1307 struts. In this example, the hinge region is formed by an anchor arm 1323 on the end of the upper struts, passing through an eye/loop 1313' at the free ends of the lower struts.

Figure 14A:
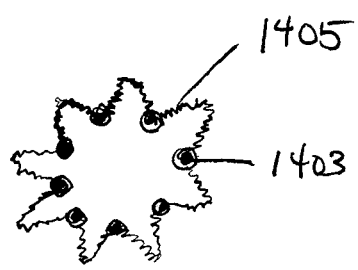
FIG. 14A is a cross-section though the collapsed implant in which the partitioning element (membrane) has been folded between adjacent struts.
Figure 14B:
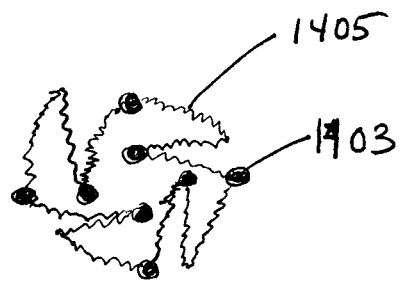
FIG. 14B shows another variation of a collapsed implant having an alternative folding configuration and associated arrangement of struts.

In any of the devices described herein, the partitioning element may be a membrane or surface (which may be flexible) that is coupled to struts. When the implant is in the collapsed configuration the partitioning element may be folded or collapsed around the struts so that the profile of the implant is sufficiently small. For example, FIG. 14A shows an implant in which the membrane (partitioning element) 1405 has been folded between adjacent struts 1403. Thus, there are pleats in the membrane at the deployed diameter, which may remain pleated or irregular in configuration even when the implant is deployed. Alternatively in some variations, the struts and any attached membrane may be arranged so that any pleats are hidden by the arrangement of the struts 1403, so that any pleats that remain in the expanded configuration are pressed between the ventricle wall and implant, behind the face of the membrane that is exposed to the active portion of the ventricle. FIG. 14B illustrates one variation in which adjacent pairs of struts are arranged so that one of the struts is behind another strut, with the excess membrane region folded behind the device. Alternatively, in one variation, the struts are arranged so that alternate strut pairs cross each other scissor-like. This crossing configuration may keep the membrane pleat behind the adjacent, fully exposed section of the membrane, while allowing the strut to uncross, deploying the extra membrane material should it be needed to reach the deployed diameter of the device.

Figure 15:
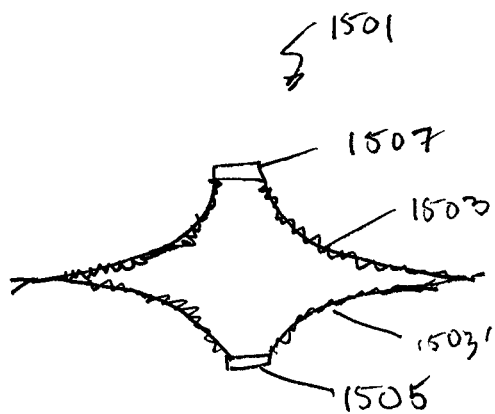
FIG. 15 shows a schematic cross-section through one variation of a ventricular volume-reduction implant.

FIG. 15 illustrates another variation of an implant having an upper frame with an upper membrane 1503, and a lower frame with a lower membrane 1503'. The upper frame has a proximal hub 1507 and the lower frame has a distal hub 1505. This variation may contact the walls of the ventricle only at the membrane perimeter, avoiding the need for foot, and avoiding interference with apical structures. In this example, both the upper and lower frames have anchors at the ends of the struts, which terminate in barbs. The upper and lower frames may be connected via a mechanical interlock or simply bonded together during a lamination process.

FIG. 16 illustrates one variation of a device in which the partitioning element is supported by an expandable frame that is formed from an inflatable region(s) of the membrane forming the partitioning element. In this example, the implant includes an upper and lower membrane that are laminated together with an inflatable region between them. The inflatable region is patterned so that the "struts" are inflatable channels connected around the periphery by the edge of the device. During delivery, the channels are empty, providing a very low profile. Once within the ventricle, the channels may be filled using a one-way fill valve. Filling the channels causes the structures to assume the shape shown in FIG. 16, and pressurizing the channels provides rigidity to the overall structure. Alternatively, the implant may be filled with a hardenable material.

Any of the variations described herein may also include one or more locating struts which is visualizable (e.g., under fluoroscopy). Asymmetric implants (e.g., having one side that is shorter than another) may particularly benefit from locating struts, which may help orient the implant within the body. For example, one or more struts could be configured to be extended from the delivery system before the others. One or more of the struts could be treated to increase the radiopacity, e.g., by gold plating. Once exposed, the locating strut or struts could be used to orient the implant. For example, the locating strut could be placed at the papillary muscle so that the short side of the implant (in an asymmetric implant) falls at the papillary muscle. In general, the implant may be marked for visualization.

FIGS. 17A and 17B show one variation of a ventricular volume-reducing implant in which the implants are self-tapping. In this example, the struts 1705 are spirally shaped around the central longitudinal axis so that as the implant is deployed near the apex of the heart the anchors on the distal ends of the struts will set into the walls of the ventricle and the foot of the implant will be forced towards the apex of the heart. As in any of the variations described above, a partitioning element (e.g., membrane 1703) may be coupled to a portion of the struts to partition the ventricle and thereby reduce its volume.

Figure 18A:
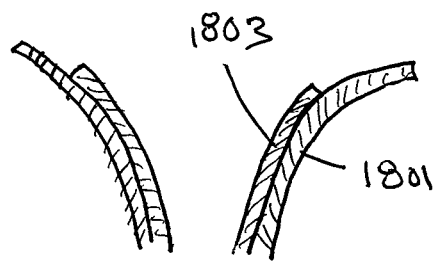
FIG. 18A shows a sectional view of a portion of an implant forming two strut regions.
Figure 18B:
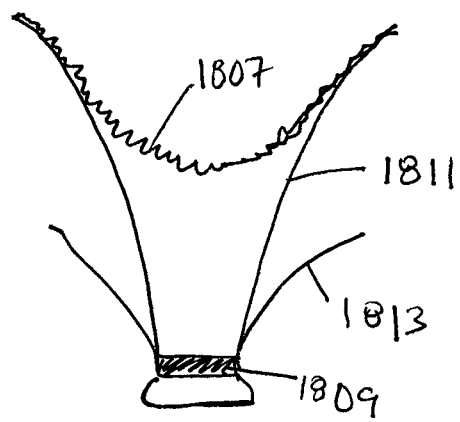
FIG. 18B shows a schematic cross-section through one variation of a ventricular volume-reduction implant incorporating the leaf-spring construction shown in FIG. 18A.

In some variations of the devices described herein the implant is formed from a plurality of tubes that are concentrically arranged and then cut (e.g., laser cut) to form the frame. This may allow relatively thinner struts to be formed compared to single-tube constructions. For example, FIG. 18 shows a variation in which the outer tube 1801 forms some of the struts while the inner tube 1803 forms additional struts. This leaf-spring construction may be formed so that the individual tubes experience much lower or lesser strains during shape-setting and device delivery, since for any geometry, the thinner leaf will have a lower stain that a thicker leaf. The lower stain could also enhance the fatigue life of the implant. This technique may also allow for an increased number of struts per implant. For example, FIG. 18B illustrates one variation of an implant that may be formed as descried, including two sets of struts 1811 and 1813 that could be cut from inner and outer tubes, respectively. The implant may also include a membrane 1807 and hub 1809.

In many of the variations described herein the partitioning element is a membrane formed of a material such as ePTFE which is secured to one or more region of the struts. Binding of the material such as ePTFE to the metal (e.g., Nitinol) struts may be a challenge. In some variations, the binding to the end regions of the struts is enhanced by providing cut-out regions in the strut that allow thicker bonding regions. This is illustrated in FIGS. 19A and 19B. For example, the eyelet region at the end of the struts provides an area for the HDPE that bonds the membrane to the strut to melt into and provide a strong mechanical bond. This in turn provides a stop for the anchor, limiting the distance it can penetrate into the tissue. FIG. 19A shows a variation in which the end of the strut includes a "wavy" region into which the material may bond. Alternately, FIG. 19B shows a strut with a cut-away region into which the material may bond.

In general, in variations in which the membrane is formed by laminating or heat-securing a flat layer of material to a wire frame (e.g., Nitinol), the membrane may be cut out of a sheet of material. For example, in some variations the frame may be sandwiched between two layers of material having different properties. In one variation the outer layer of material forming the partitioning element is a sheet of ePTFE that is optimized for tissue in-growth and the inner layer of material forming the partitioning element is a sheet of ePTFE optimized for hydraulic load (e.g., having a high creep resistance). Thus, the ePTFE facing the active region of the ventricle is configured to tissue in-growth, while the region facing the static chamber is optimized for hydraulic loading, providing a fluid barrier and resistance to creed effects caused by long-term loading.

Alternatively, in some variations the membrane may be formed on the implant by dip coating the frame 2001 after it has been connected to a polished mandrel 2003, as illustrated in FIG. 20. For example, high durometer Pebax may be dissolved in tetrahydroforan. The frame may then be mounted on a fined finished mandrel and repeated dip coated into the Pebax/THF solution. The THF solution may be removed (or allowed to separate out) leaving behind a thin Pebax layer. The device may be dipped after removing the mandrel as well.

Figure 21A:
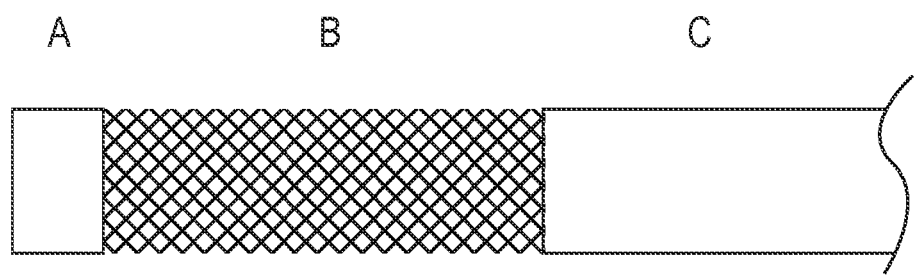
FIGS. 21A and 21B illustrate a retrieving device for retrieving a deployed implant, and a method of retrieving an implant (FIG. 21B).
Figure 21B:
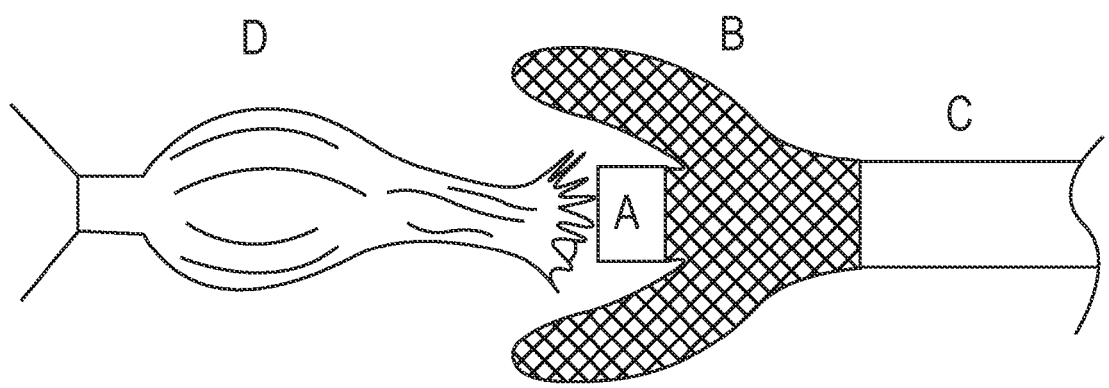

Any of the variations described herein may also be retrievable, and may be configured for use with a retrieving element. For example, FIGS. 21A and 21B illustrate one variation of a retrieving element configured as a prolapsing guide. In this example, the guide is configured to remove the implant after collapsing the implant from the expanded and deployed configuration. The implant is safely retrieved by covering the sharp points of the collapsed struts and membrane, enable the device to be atraumatically removed from the patient's ventricle and aorta, and allowing simple surgical remove from the iliac artery. In FIG. 21A, the guide includes three parts, A, B and C. Part A in FIG. 21A is a radiopaque marker band, and part B is a flexible braided region. Part C is the elongate shaft portion of the device. FIG. 21B illustrates the operation of the device. The braided region B underlies the distal potion of the access catheter; the braid is fused to itself and to the marker band, A. The braid region may also be encapsulated in a polymer matrix at C, while the region under B is unconstrained.

In operation, an implant may be removed after collapsing the implant (e.g., by pulling on a string or other element configured to collapse the expanded implant) by drawing the implant against the distal tip of the prolapsing guide catheter, allowing the distal end of the catheter to collapse around the proximal end of the collapsed implant, as shown in FIG. 21B, surrounding the anchoring members on the ends of the struts, as shown. The implant may then be safely removed and withdrawn from the ventricle and aorta. As mentioned above, the implant may be configured for collapse by pulling on a string. The string may be secured around the edge (periphery) of the implant. In some variations a sting or suture is included connected to a more central region of the implant which may allow the implant to be more easily withdrawn after insertion and collapse. For example, a centrally attached suture or string may be connected to a central cross-bar within the body or hub of the implant. The ends of the string or suture may be held within the delivery device, and manipulated to retrieve the implant, or, if the implant is desirably positioned and deployed, withdrawn from the device. This second (or central) string may allow the implant to be place within the ventricle and temporarily released from the delivery system.

Figure 22A:
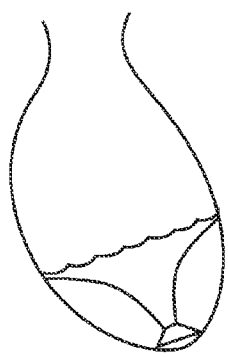
FIGS. 22A-22I illustrate one method of retrieve a deployed implant.
Figure 22B:
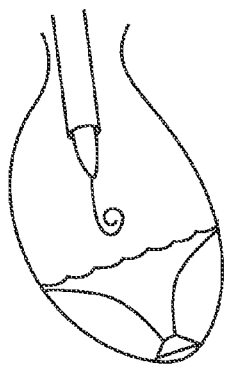
Figure 22C:
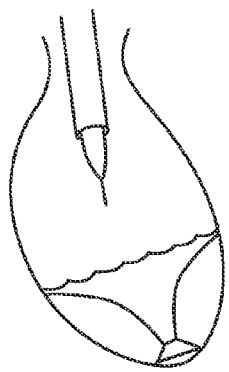
Figure 22D:
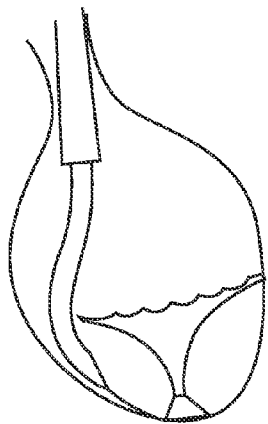
Figure 22E:
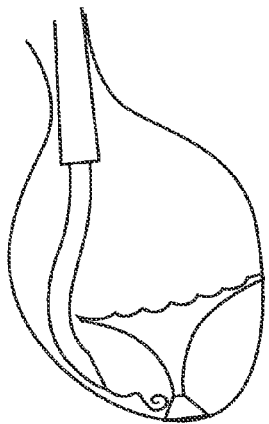
Figure 22F:
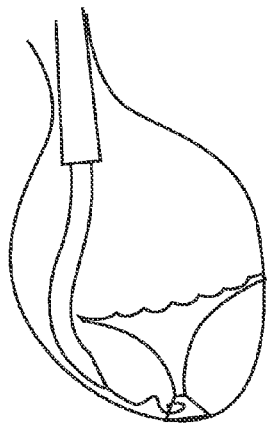
Figure 22G:
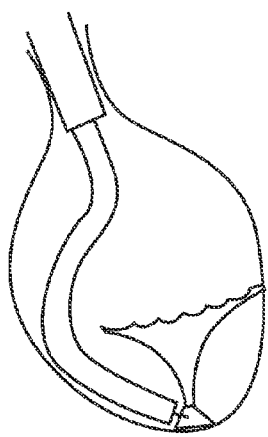
Figure 22H:
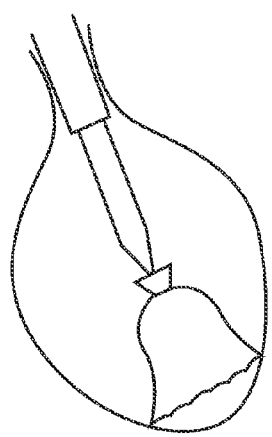
Figure 22I:
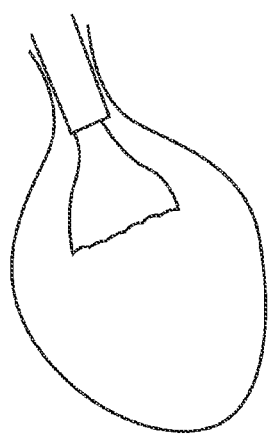

FIGS. 22A-22I illustrate one variation of a method for retrieval of an implant. In this variation, a fully deployed implant (deployed in the ventricle) is removed by first inserting (FIGS. 22C) a retrieval tool having a hook for grasping the apical region (distal end) of the implant between the wall of the ventricle and the implant, as shown in FIGS. 22D and 22E. The hook may be extended to engage the distal end as shown in FIG. 22F. Finally the implant may be secured to the retrieval device and pulled from the ventricle, as shown in FIG. 22H and 22I.

Figure 23A:
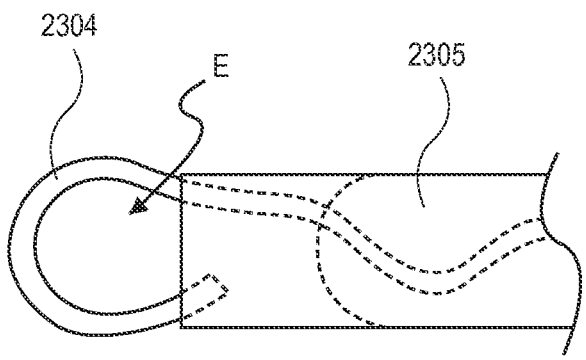
FIGS. 23A-23E illustrate a device for retrieving an implant, including a hook and catheter.
Figure 23B:
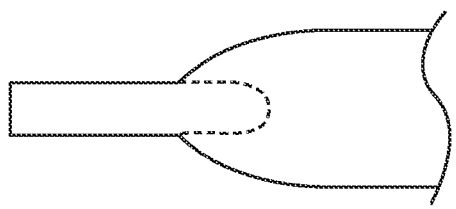
Figure 23C:
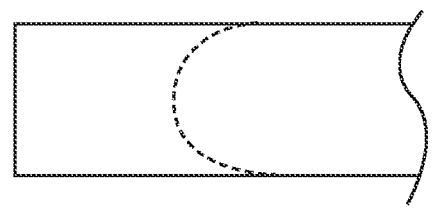
Figure 23D:
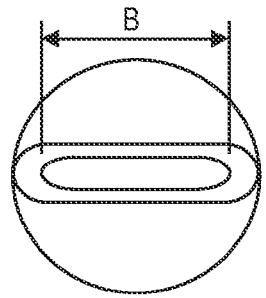
Figure 23E:
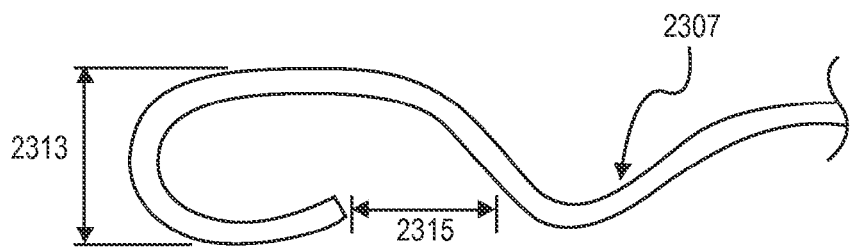

FIGS. 23A-23E illustrate one variation of a retrieval catheter including a hook that may be withdrawn into a protective catheter sheath. For example, FIG. 23A shows the hook region 2304 extending from the sheath 2305. FIGS. 23B and 23C show side and top views of the sheath for the hook, respectively. FIG. 23D shows an end view of the sheath, and FIG. 23E shows a side view of a hook. The hook may be a simple round wire including an alignment curve 2307 that keeps the hold aligned within the slot of the sheath. The width of the opening 2313 may be configured so that the hook is sufficiently wide to allow grasping of the implant without preventing it from rotating, which may help disengage the implant from the tissue.

Figure 24A:
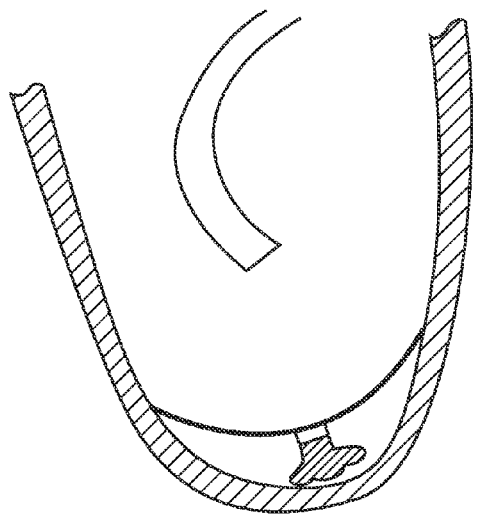
FIGS. 24A-24F illustrate a method of retrieving a deployed implant.
Figure 24B:
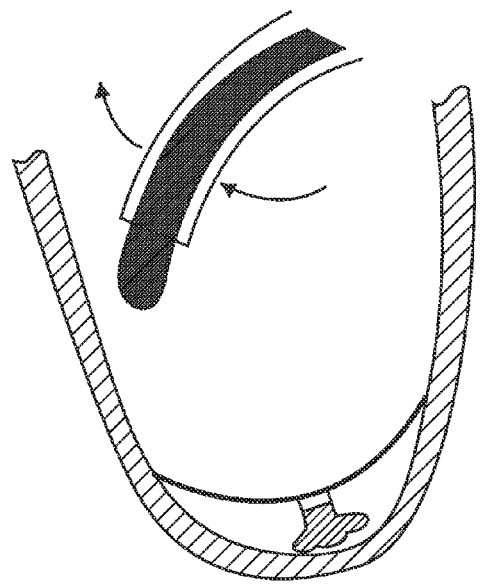
Figure 24C:
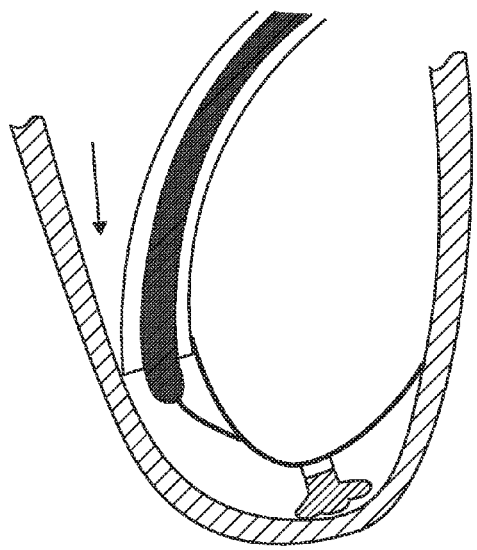
Figure 24D:
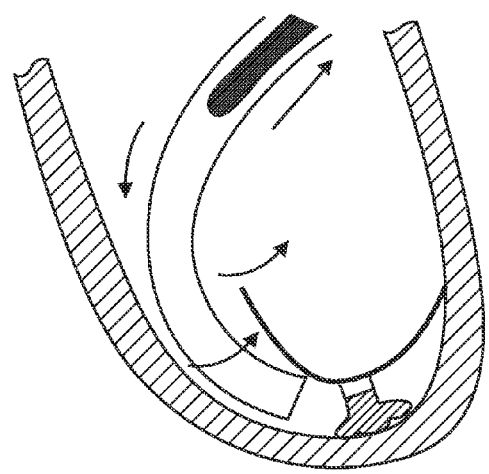
Figures 24E, 24F:
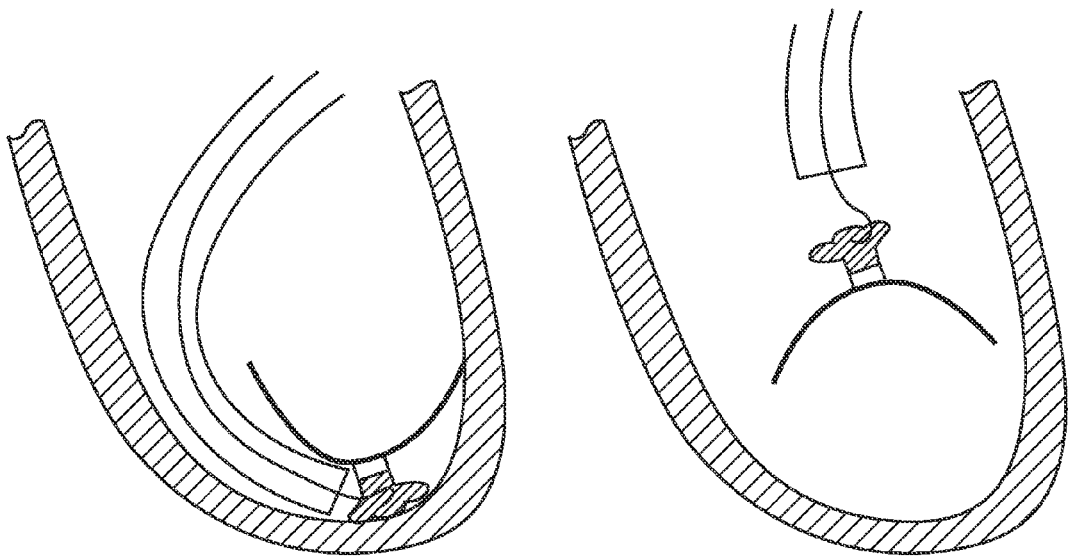

Another variation of an implant retrieval device is shown in FIGS. 24A-24F. The retrieval device in FIGS. 24A-24F is operated similarly to the sheathed hook retrieval device illustrated in FIGS. 23A-23E. The retrieval device in FIGS. 24A-24F include a pre-curved catheter that may be straightened using a stiffener as shown in FIGS. 24B and 24C. After the catheter opening is positioned behind the implant, as shown in FIG. 24D, the stiffener can be withdrawn and a removal element including a hooking element can be inserted using the catheter, as shown in FIG. 24E and used to hook and remove the implant, as shown in FIG. 24F.

Figure 25A:
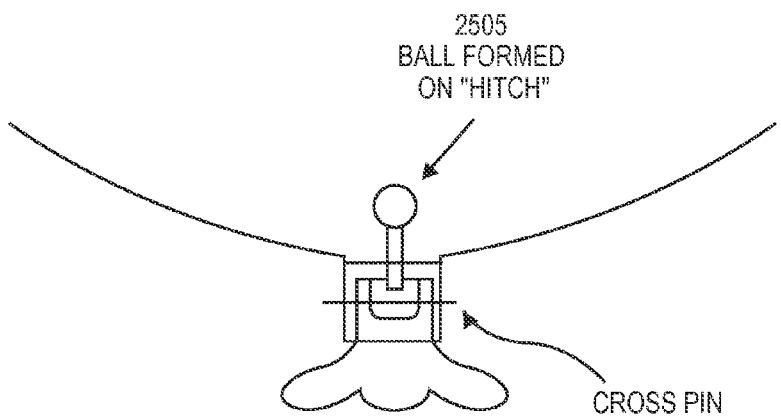
FIG. 25A shows a schematic cross-section through one variation of a ventricular volume-reduction implant including a removal element (shown as a ball or hitch formation in this example).
Figure 25D:
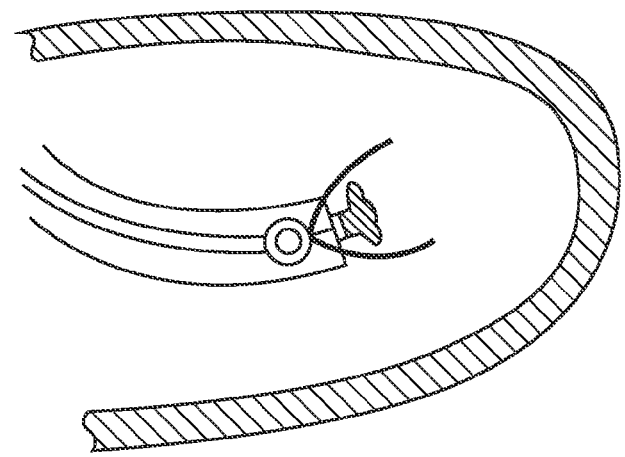
FIGS. 25B-25D illustrate removal of an implant such as the one shown in FIG. 25A using the removal element.
Figure 25C:
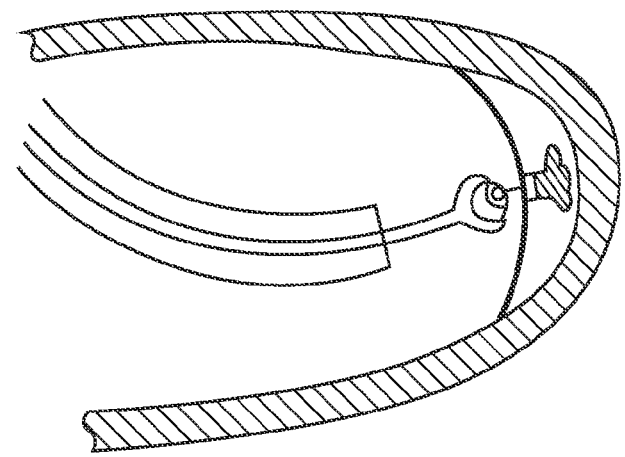
Figure 25B:
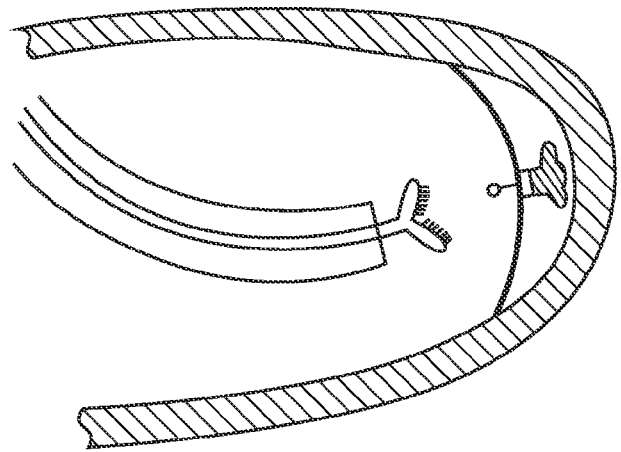

In some variations, the ventricular volume reduction implant may be adapted to include a removal element that facilitates removal of the implant after insertion. For example, FIG. 25A illustrates an implant with a removal feature. In this variation, the removal feature is a 'trailer hitch' formed as a ball joint 2505 in the central region of the implant. This hitch may be used to remove the implant after insertion. For example, a pair of biopsy forceps may be used to grab the hitch and retrieve the implant. The hitch could be attached to the implant in any one of several ways. In some variations the hitch is integral to the frame. FIGS. 25B-25C illustrate one method of removal of an implant including a hitch. In FIG. 25B a gripping forceps is used within a catheter and guided to the implant, where it is used to grasp the hitch, as shown in FIG. 25C. The implant may then be pulled at least partially into the catheter to collapse it, as shown in FIG. 25D, and thereafter remove the implant from the ventricle.

Other device and system for removal of an implanted device, or for "bailout" (stopping and removing a device during the insertion procedure) are also contemplated. For example, an implant may include a suture or ring (e.g., a Nitinol ring) around the outer perimeter as previously described. A removal device may include a hook or grasper for engaging the ring or suture to constrict the outer rim of the device, collapsing it back into the condensed form.

In general, before insertion of an implant into a ventricle, the practitioner (e.g., surgeon) may determine what size implant would best work in the ventricle to appropriately reduce the ventricular volume. Thus, one or more sizers or sizing techniques may be used. In some variation, sizing of the implant is performed using analysis of angiographic and/or other imaging techniques such as ultrasound. Visualization data may then be used to identify the height and diameter of the implantation zone within the ventricle and therefore the proper size and/or shape of the implant to be used. In performing this step, it would be useful to have one or more sizers that could be used to provide reference when examining the heart to determine the orientation, size and morphology of the implant to be used to reduce ventricular volume.

Figure 26A:
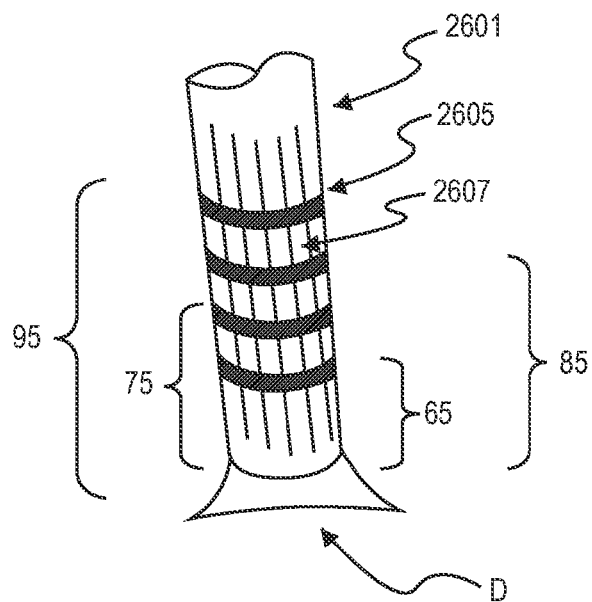
FIGS. 26A and 26B show one variation of a sizer device for determining the approximate dimensions of the region of a ventricle into which an implant (e.g., a volume-reducing implant) may be inserted.
Figure 26B:
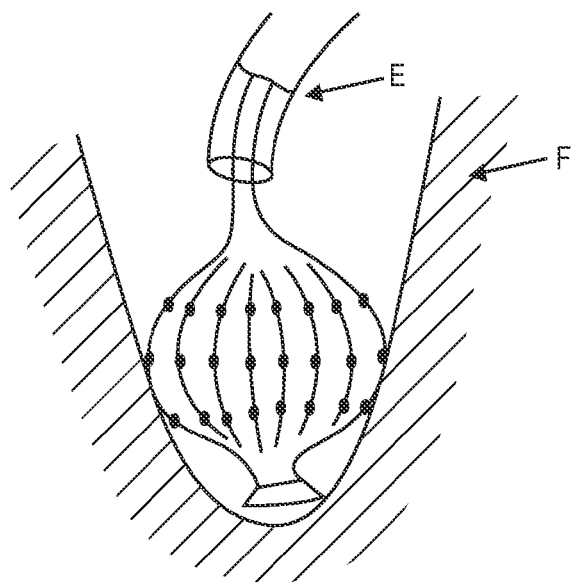

In one variation, a sizer device comprises an expandable frame (similar to the implant frames described above) having a plurality of radiopaque bands or other markers for visualization of the outer perimeter of the sizer. FIG. 26A shows one variation of such as device. The bands are separated from each other a known or predetermined distance (illustrated as 65, 75, 85 or 95 mm from the bottom of the device in this example). The sizer may be formed from a Nitinol tube 2601 having a plurality of calibrated radiopaque bands 2605 and a plurality of longitudinal slits 2607 that allow the device to expand outwards as shown in FIG. 26B. In operation, the sizer may be expanded within the apical region of the ventricle, and the user may then note which radiographic markers contact the ventricle within the desired landing zone. The user may also easily detect the presence of any ventricular structures that would impede proper deployment of an implant, as the sizer struts would also not deploy properly. Once the sizing operation is complete, the user may retract the sizer into a guide catheter, collapsing it. The sizer can then be removed and an implant inserted (using the same guide, if desired).

In some variation of the sizer describe above, the sizer expansion is limited by cross-struts 2609 to prevent over expansion within the ventricle, as shown in FIG. 26C.

In some variations, the sizer is configured so that expansion and collapse are controlled by controlling the proximal and distal ends of the expandable region, as shown by FIG. 27. For example, the central region of the sizer may include a rod 2705 that moves coaxially with an outer catheter 2703; the distal end of the rod may be attached to the distal end of the sizer (e.g., near the foot) while the distal end of the catheter may be coupled or continuous with the proximal end of the expandable region 2701 of the sizer. Pushing distally on the catheter may cause the sizer to expand as the proximal end is brought near the distal end. In some variations the sizer may also include a rotatable joint near the expandable region, allowing the expandable sizer region 2701 to be rotated, e.g., by rotating the inner rod 2705, which may be a torqueable member.

Figure 29A:
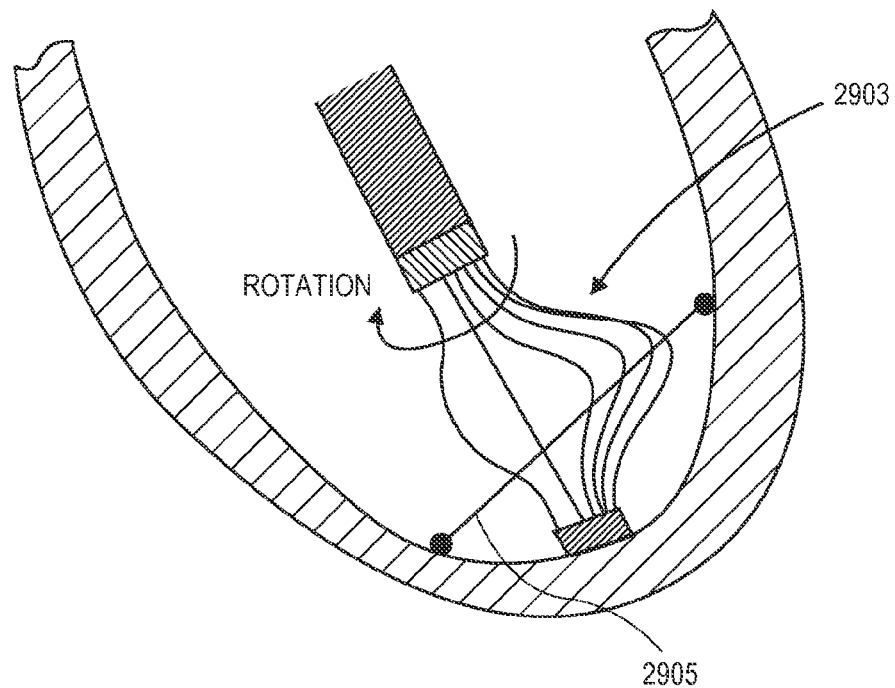
FIGS. 29A and 29B show side and top views, respectively, of a sizer such as the sizer shown in FIG. 26A being used to determine the dimensions of a region of the ventricle.
Figure 29B:
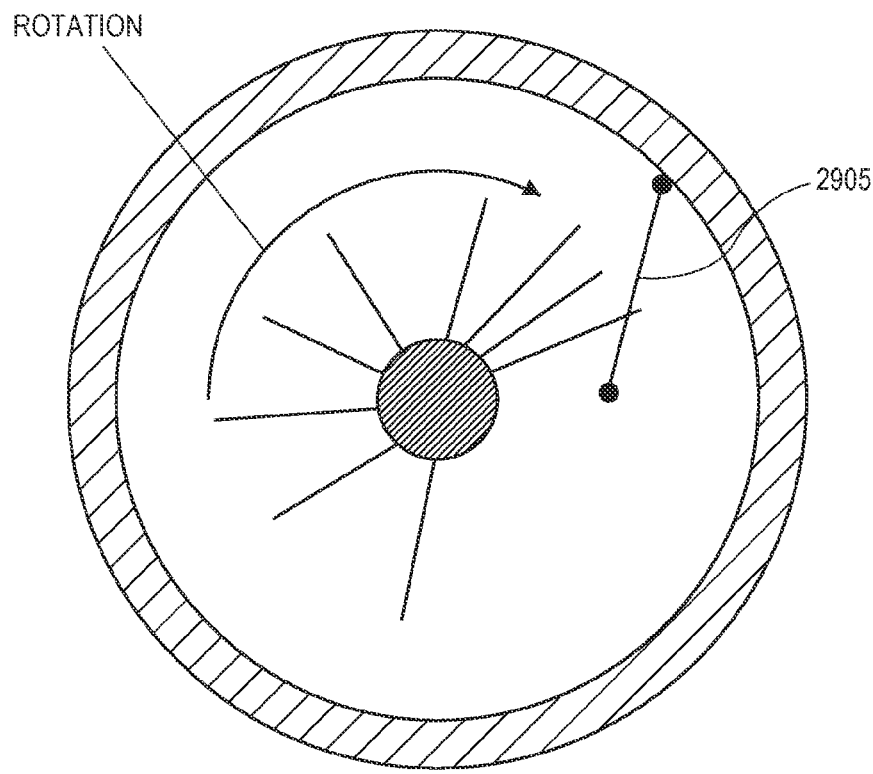

Rotation of the sizer may be particularly helpful for determining the location of structures like chords that extend across region of the ventricle, but are not typically visible under most visualization techniques. FIGS. 29A and 29b illustrate how rotation of the sizer may help identify the presence of a chord extending across the ventricle. For example, rotation of a sizer (e.g., by rotating the inner rod member as described above) may cause the spokes to "bunch up" 2903 against a chord 2905. FIG. 29A shows side view of a sizer being rotated within a ventricle while FIG. 29B shows a top view. In this example, a chord extends between the walls of the ventricle; as the sizer is rotated, the struts bunch up against the chord, indicating approximately where it is located.

In some variations the sizer is per-biased or shape-set into the expanded form. For example, the sizer may be shape-set into a rounded form as shown in FIG. 28.

Figure 30:
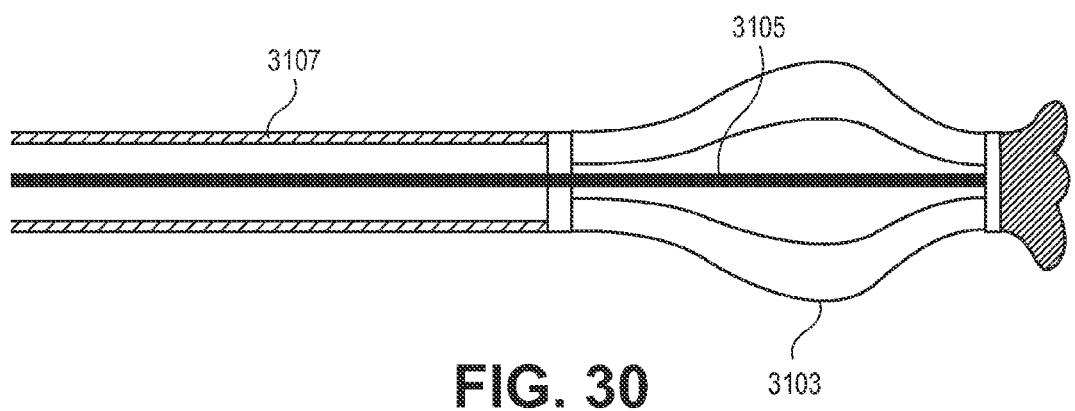
FIG. 30 shows one variation of a sizer.
Figure 31:
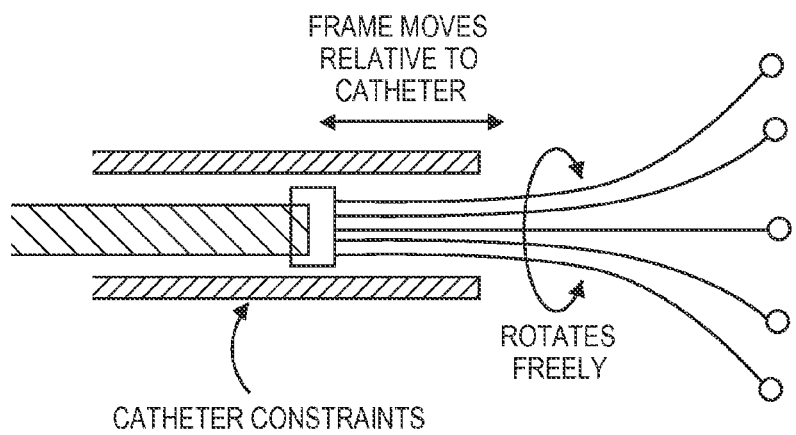
FIG. 31 shows one variation of a sizer.

FIGS. 30 and 31 illustrate different variations of sizers that may be used. For example, in FIG. 30, the sizer is formed by an expandable frame 3103 that directly attaches to a smaller OD torque member 3107. A mandrel (rod) 3105 runs through the frame and attaches to a foot of the frame. Pushing on the proximal end of the mandrel collapses the frame. Torquing the outside torque member rotates the whole assembly. The entire assembly may pass through a guide catheter (not shown). The torque shaft 3107 may be covered in polymer or other lubricious material to reduce friction.

In FIG. 31, the sizer includes a plurality of expandable struts having atraumatic distal tips that can "fan out" from a catheter opening. The atraumatic tips and/or the entire (or a sub-region of the) strut may be radiopaque. For example, the frame could be made of a laser cut tube welded or soldered to a torque member, or it could be a series of heat-set wires spot welded to the torque member. The struts could be configured (e.g., by heat setting) to expand to a constant max OD, or they could be configured to continue to expand outwards as the struts are pushed out of the end of the catheter.

Figure 32:
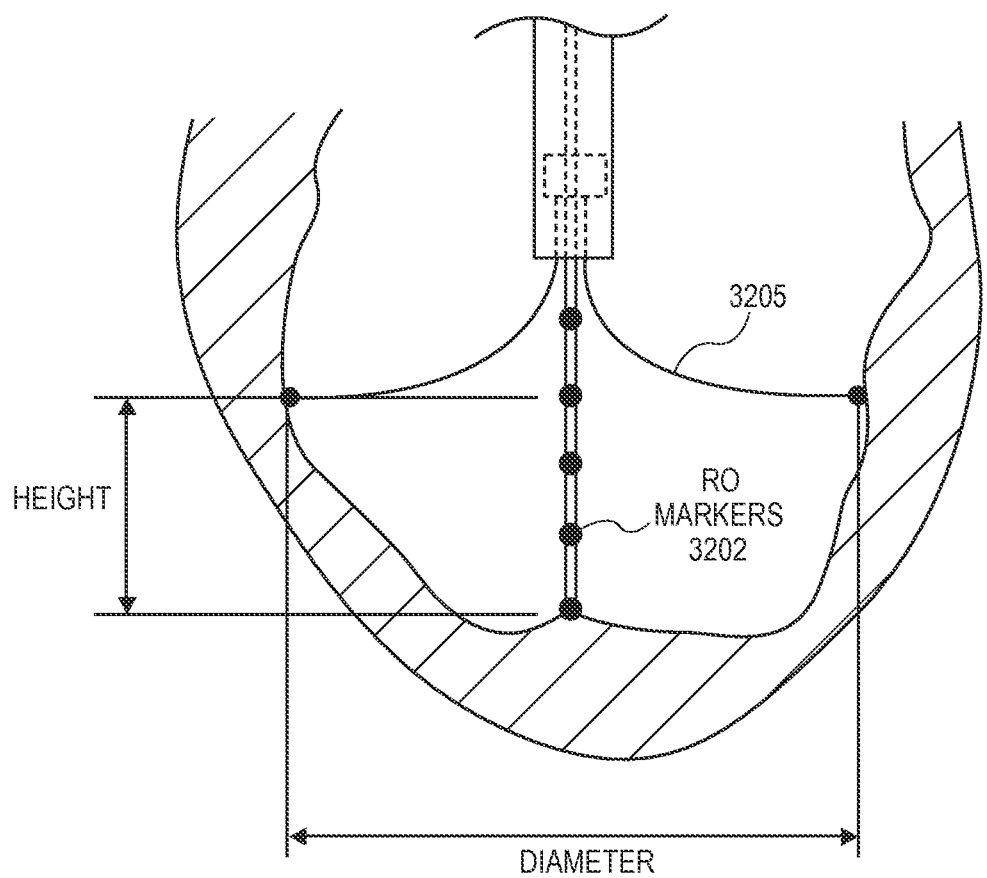
FIG. 32 shows one variation of a sizer deployed into a ventricle.

In some variations, the sizer may include a separate or integral depth measuring element. For example, FIG. 32 illustrates one variation of a sizer similar to the variation shown in FIG. 31, in which a center strut has multiple "depth" indicators and is not pre-biased or configured to bend or curve upon exiting the catheter. Thus, the central region may include radiopaque markers 3202 that extend down from the catheter. The separation of this line of markers may be known and constant. In addition, struts may cure outwards 3205 to indicate the width or diameter of the region. By increasing the number of struts extending from the catheter, increasingly detailed '3D' representations of the ventricle may be determined.

Although the methods and systems described above may include a separate sizer to be used prior to implantation of the ventricular volume reduction implant, in some variations the implant may include an integral sizer. For example, the distal tip of the implant may include a sizer that is configured to be used prior to fully deploying the implant. In one variation a sizer balloon at the distal tip region (the "foot region") of an implant may be inflated to determine (by contact with ventricle wall and landing zone) the configuration of the ventricular landing zone prior to fully deploying the implant. The balloon may be filled with a radiopaque material.

Figure 33A:
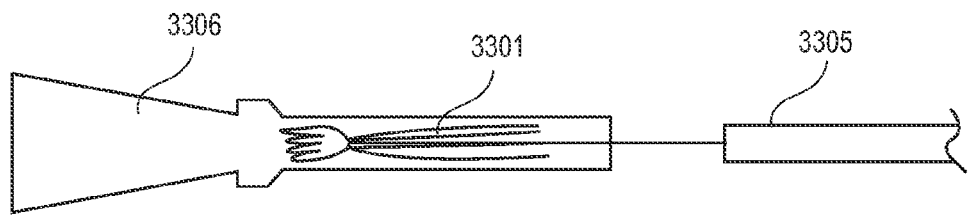
FIGS. 33A-33D illustrate a method of flushing an implant prior to implantation.

In general, the implants described herein may be flushed with fluid (e.g., saline) prior to implantation, and bubbles (air bubbles) may be removed. It may be desired to flush the device in an end-to-end rather than from a port in the middle of the sleeve. One difficult area to flush is the inside of the implant near the balloon. This region may be flushed by including a temporary or permanent flush port to the center of the implant, as illustrated in FIGS. 33A-D. FIG. 33A shows the implant 3301 loaded using a funnel 3306, where the implant has been coupled to the end of a delivery catheter 3305. The implant may be loaded into a sleeve (not shown).

Figure 33B:
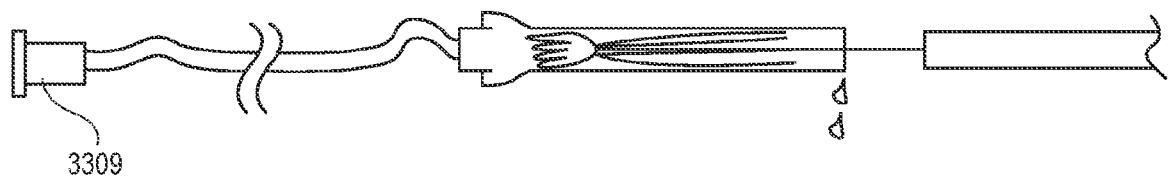
Figure 33C:
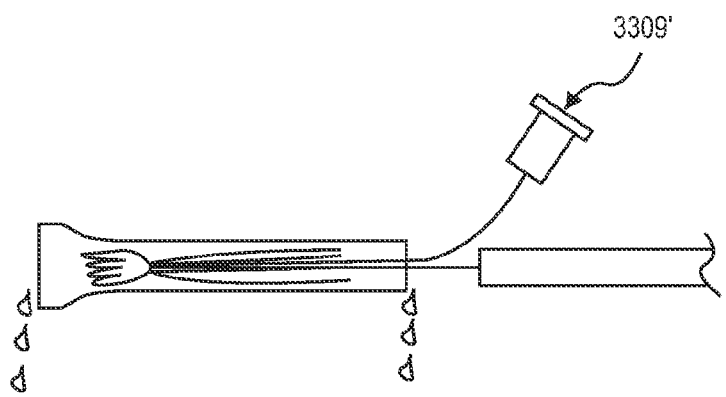
Figure 33D:
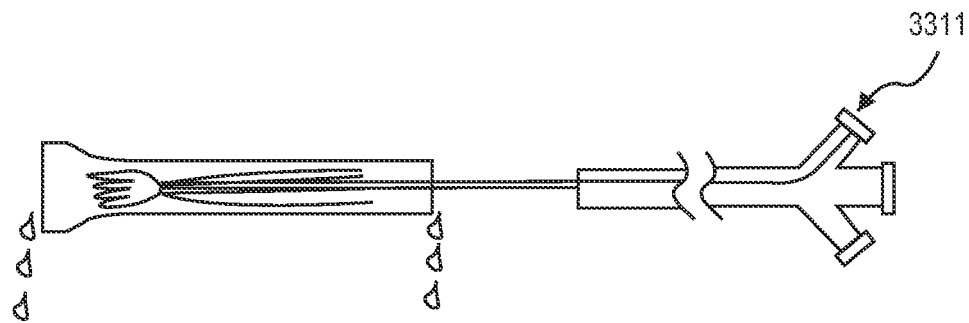

The implant may then be flushed by attaching a flushing port 3309 at the distal end, as shown in FIG. 33B, or at the proximal end 3309' as shown in FIG. 33C, or using a permanent flush port 3311 at the proximal end, as shown in FIG. 33D.

Figure 34A:
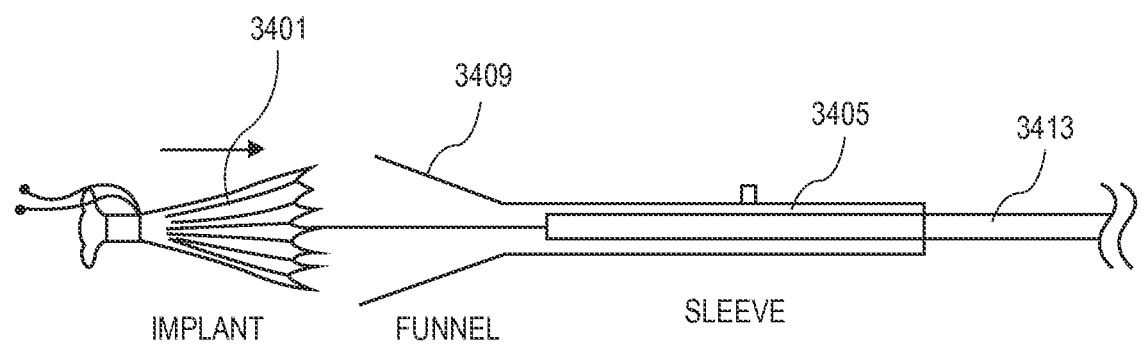
FIGS. 34A-34C illustrate a method of flushing an implant prior to implantation.
Figure 34B:
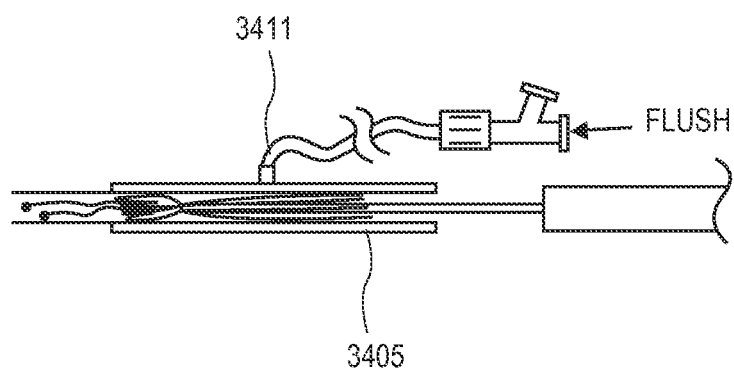
Figure 34C:
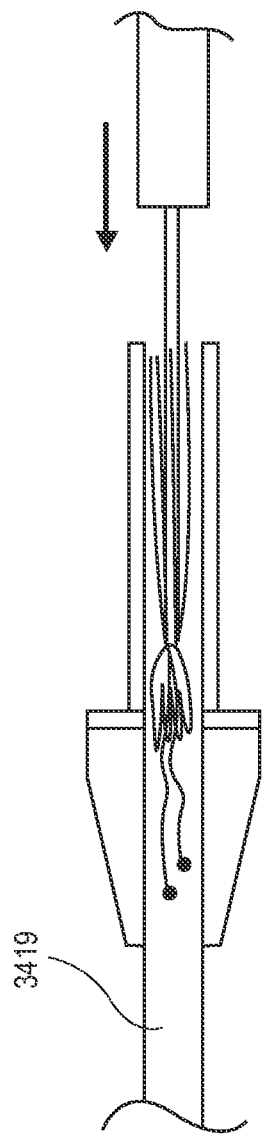

In some variations, the implant is loaded in to a sleeve, as mentioned. For example, FIGS. 34A-34C illustrate the use of a loading sleeve that can be used to flush the implant before implantation. In FIG. 34A the implant 3401 is loaded into a sleeve 3405 using a loading funnel 3409. The implant has been attached to the delivery catheter 3413 prior to loading and flushing, as shown. FIG. 34B shows the implant 3401 loaded into the sleeve, which is then flushed with fluid (e.g., saline) from the flushing port 3411 on the sleeve 3405. Finally, in FIG. 34C, the implant and sleeve are inserted directly into the access catheter 3419 and the implant may be introduced into the patient.

Figure 35:
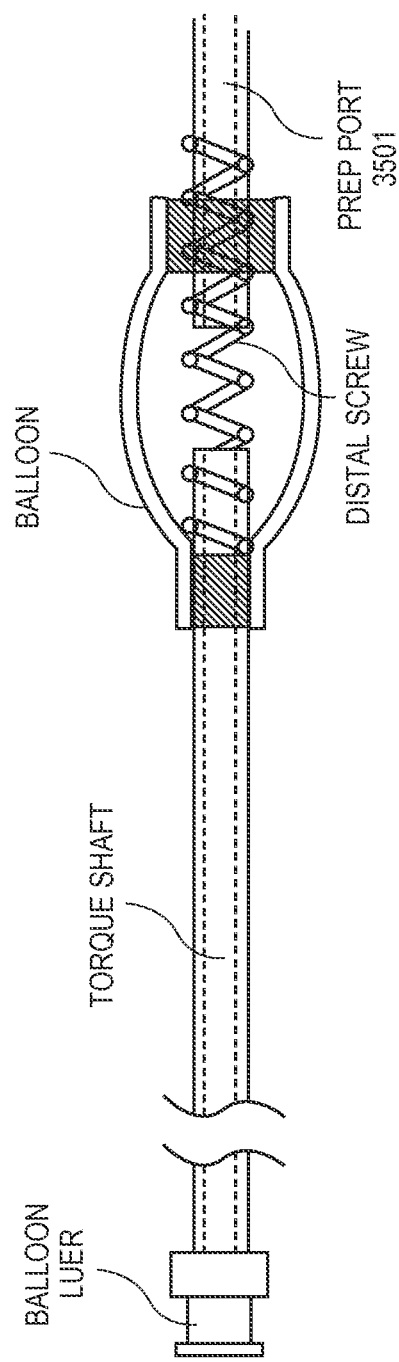
FIG. 35 illustrates one variation of an inserter/applicator for inserting and deploying a volume-reducing implant.

In variations in which the delivery device includes a balloon (e.g., to help expand the implant when inserted into the ventricle) or where the implant itself includes a balloon (e.g., as a foot region, strut, etc.), the balloon may be pre-filled with inflation fluid. This may avoid bubbles or filling irregularities. For example, in variations of devices and system including balloons, the implant may include a "prep port" that can be opened on one region of the inflatable member, from which fluid (e.g., saline) may be drawn. FIG. 35 shows one variation of an inserter with a balloon expander that includes a prep port 3501. The device with the balloon (e.g., inserter, implant, etc.) can be immersed in saline, and a vacuum applied at one end until air is purged from the system. Fluid (in this example, saline) can be drawn in from the prep port. A small amount of saline may then be injected back through the system, further helping to eliminate air bubbles and positively pressurizing the system so that air does not seep in when the balloon is removed from the saline.

Figure 36A:
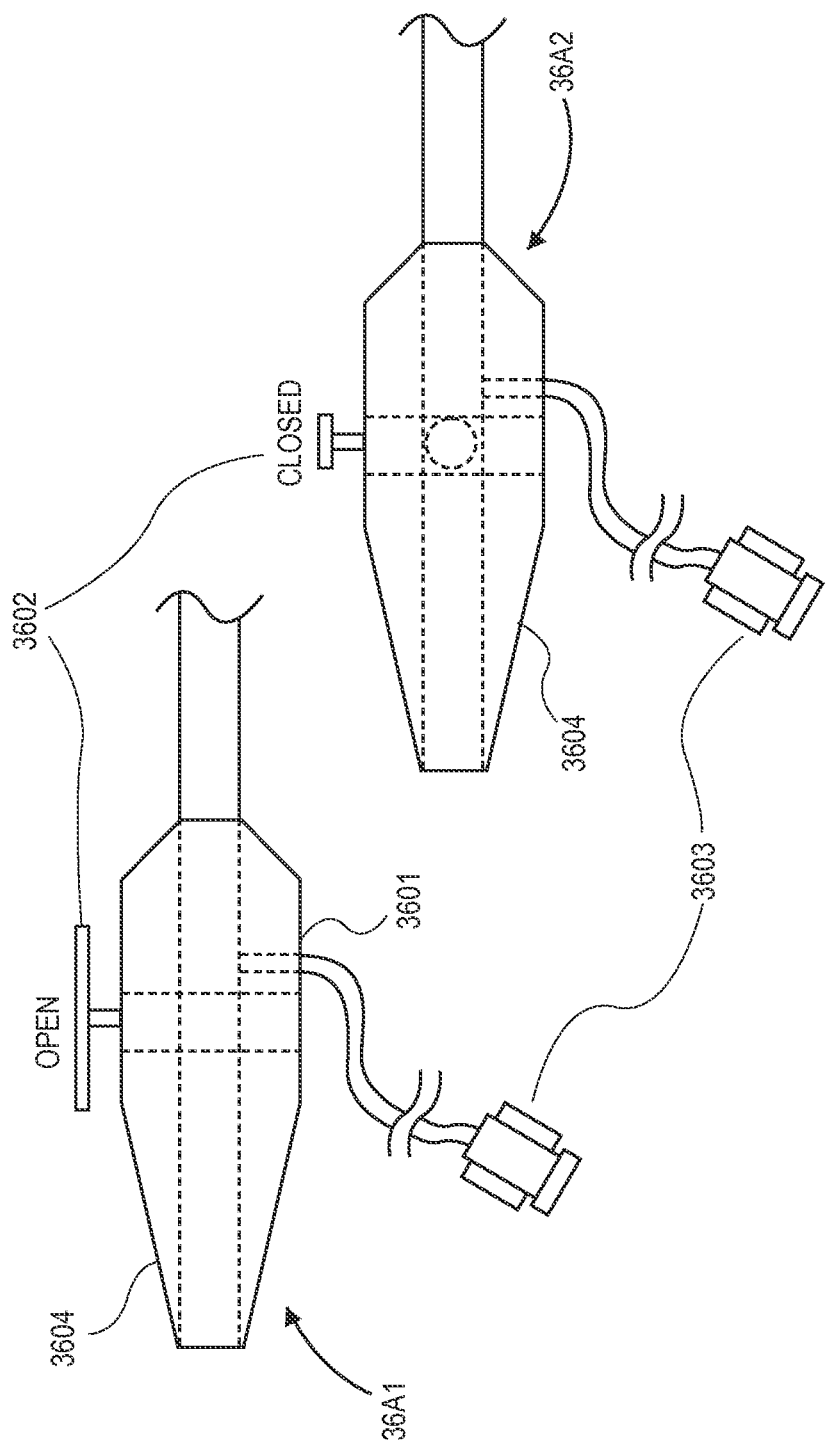

FIGS. 36A-36F illustrate another variation of method and system for loading an implant into a guide catheter for implantation. For example, FIG. 36A shows two views of a guide catheter handle; FIG. 36A1 shows the handle with a valve 3602 open, and FIG. 36A2 shows the handle with the side valve 3602 closed. The guide catheter handle shown has a side port 3603 that may be used for flushing and black-bleeding. The valve 3602 may be operated in a manner similar to a stopcock. The bore of the valve may be large enough o allow the implant to pass when in its collapsed state. The proximal portion of the guide catheter handle 3604 may be made to interfere with and attach to an implant loader 3606, which is shown in FIG. 36B. in this example, one exemplary implant 3607 is loaded onto a delivery catheter 3605 and collapsed into the implant loader 3606. The implant loader includes an implant loader seal 3608 at the proximal end.

With the implant 3607 collapsed inside the implant loader 3606, the implant loader can be attached to the proximal portion of a guide catheter handle 3604, as shown in FIG. 36C. The valve 3602 can then be opened and the implant loader seal 3608 be sealed around the delivery catheter to control back bleeding. The implant may then be advanced into the guide catheter. Air distal to the implant may be pushed out through the side port 3603 by blood pressure as the implant is advanced. Once the implant reaches the side port, a saline bag may be attached to the side portion to allow saline to fill in proximal to the implant as the implant is advance to the left ventricle.

Figure 36D:
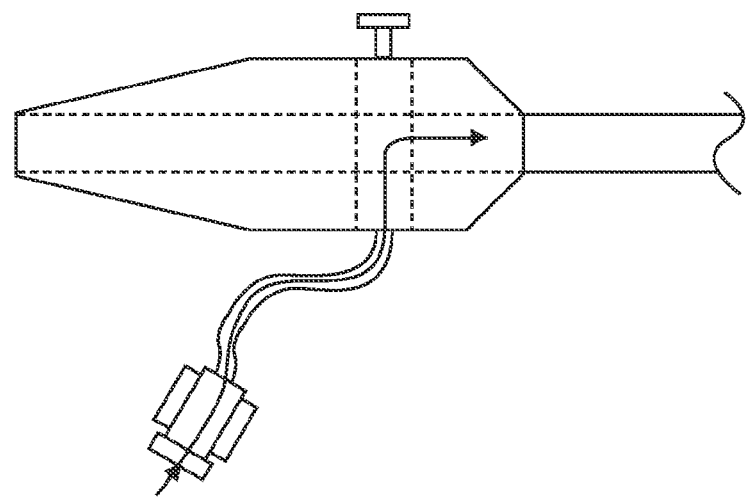
FIGS. 36D-36F show variations of operation of the handle of FIG. 36A.
Figure 36E:
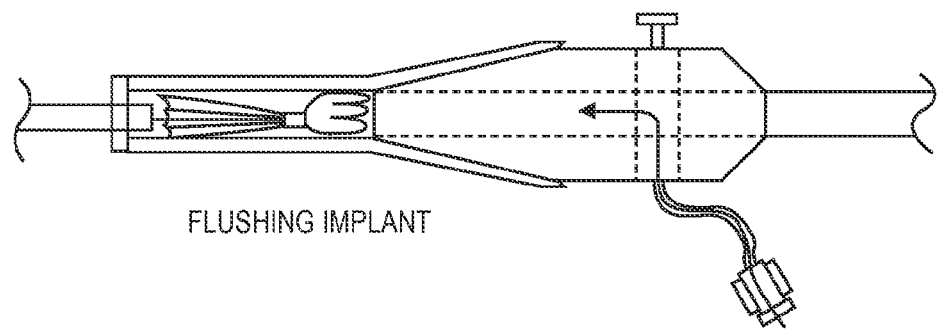
Figure 36F:
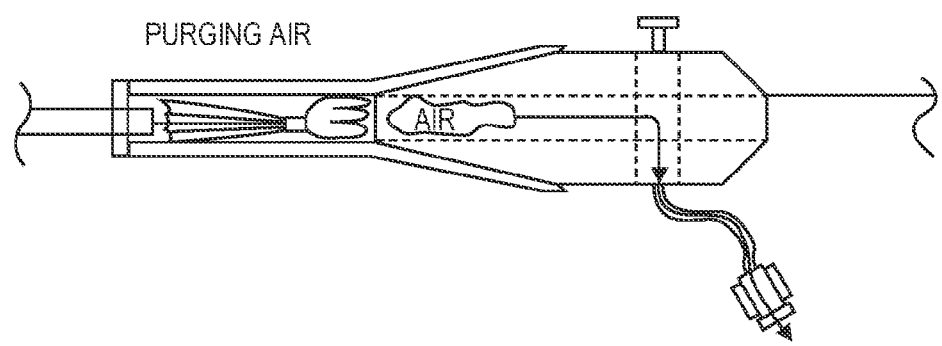

In some variations, the guide catheter handle may be configured so that the valve 3602 is used to route the flow of the side port 3603 distal or proximal of the valve. This may allow the side port to perform different functions. For example, as shown in FIG. 36D, the handle may be used to flush the catheter, or for flushing the implant, as shown in FIG. 36E, or for purging air, as shown in FIG. 36F.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

What may be claimed is:

1. A ventricular volume reduction implant for insertion into a patient's ventricle to reduce the active volume of the ventricle wherein the height of the implant can be adjusted to adjust the reduction volume, the implant comprising:
   a partitioning membrane configured to span across the ventricle to partition the ventricle; and
   a support frame comprising an adjustable-height stem region, the support frame comprises a plurality of support struts, wherein adjusting the height of the stem region adjusts the height of the partitioning membrane within the ventricle;
   wherein the adjustable-height stem region comprises a lock to lock the stem in a predetermined height, and
   wherein the implant is configured to be inserted in a collapsed configuration and expanded into a deployed configuration within the ventricle.

2. The device of claim 1, wherein the adjustable-height stem region comprises a movable collar configured to adjust the height.

3. The implant of claim 1, wherein at least one of the struts comprises a locating strut having a radiopaque marker.

4. A ventricular volume reduction implant for insertion into a patient's ventricle wherein the height of the implant can be adjusted, the implant comprising:
   a partitioning membrane configured to span across the ventricle to partition the ventricle;
   a foot region configured to be inserted near an apex of the ventricle; and
   a support frame comprising an adjustable-height stem region, wherein the support frame comprises a plurality of support struts, wherein adjusting the height of the stem region adjusts the height of the partitioning membrane relative to the foot region;
   wherein the adjustable-height stem region comprises a lock to lock the stem in a predetermined height, and
   wherein the implant is configured to be inserted in a collapsed configuration and expanded into a deployed configuration within the ventricle.

5. The device of claim 4, wherein the adjustable-height stem region comprises a movable collar configured to adjust the height.

6. The device of claim 4, wherein the lock comprises locking tabs for securing a movable collar to the stem.

7. The implant of claim 4, wherein at least one of the struts comprises a locating strut having a radiopaque marker.

8. A ventricular volume reduction implant for insertion into a patient's ventricle to reduce the active volume of the ventricle wherein the height of the implant can be adjusted to adjust the reduction volume, the implant comprising:
   a partitioning membrane configured to span across the ventricle to partition the ventricle; and a support frame comprising an adjustable-height stem region, the support frame comprises a plurality of support struts, wherein adjusting the height of the stem region adjusts the height of the partitioning membrane within the ventricle;

wherein the adjustable-height stem region comprises a movable collar configured to adjust the height, and wherein the implant is configured to be inserted in a collapsed configuration and expanded into a deployed configuration within the ventricle.

* * * * *